(12) United States Patent
Shorrosh

(10) Patent No.: US 6,537,750 B1
(45) Date of Patent: Mar. 25, 2003

(54) PLANT FATTY ACID DESATURASE PROMOTERS

(75) Inventor: Basil S. Shorrosh, Fort Collins, CO (US)

(73) Assignee: Cargill Incorporated, Wayzata, MN (US)

(*) Notice: Subject to any disclaimer, the term of this patent is extended or adjusted under 35 U.S.C. 154(b) by 0 days.

(21) Appl. No.: 09/366,715

(22) Filed: Aug. 4, 1999

Related U.S. Application Data

(60) Provisional application No. 60/095,317, filed on Aug. 4, 1998.

(51) Int. Cl.$^7$ .................................................. C12Q 1/68
(52) U.S. Cl. .......................... 435/6; 800/281; 800/298; 800/295; 800/255; 435/64.1; 435/134; 435/419; 435/430; 435/468; 435/471; 536/23.2; 426/629; 554/223; 554/224; 554/227
(58) Field of Search ................... 800/281, 298, 800/295, 255; 435/69.1, 134, 6, 419, 430, 468, 471; 536/23.2; 426/629; 554/223, 227, 224

(56) References Cited

U.S. PATENT DOCUMENTS

| | | | |
|---|---|---|---|
| 4,761,373 A | 8/1988 | Anderson et al. | |
| 4,940,835 A | 7/1990 | Shah et al. | |
| 4,987,071 A | 1/1991 | Cech et al. | |
| 5,188,958 A | 2/1993 | Moloney et al. | |
| 5,231,020 A | 7/1993 | Jorgensen et al. | |
| 5,254,678 A | 10/1993 | Haseloff et al. | |
| 5,380,831 A | 1/1995 | Adang et al. | |
| 5,489,520 A | 2/1996 | Adams et al. | |
| 5,668,299 A | 9/1997 | Debonte et al. | |
| 5,767,363 A | 6/1998 | De Silva et al. | |
| 5,850,026 A | 12/1998 | DeBonte et al. | |
| 5,925,806 A | 7/1999 | McBride et al. | |
| 6,063,947 A | * 5/2000 | DeBonte et al. | 554/223 |
| 6,075,183 A | * 6/2000 | Knutzon et al. | 800/281 |

FOREIGN PATENT DOCUMENTS

| | | |
|---|---|---|
| EP | 0 255 378 B1 | 2/1988 |
| WO | WO 98/02562 | 1/1998 |
| WO | WO 98/08963 | 3/1998 |
| WO | WO 98/29554 | 7/1998 |
| WO | WO 98/42852 | 10/1998 |
| WO | WO 98/56239 | 12/1998 |
| WO | WO 99/05265 | 2/1999 |
| WO | WO 99/24586 | 5/1999 |

OTHER PUBLICATIONS

Barta et al., "Purification and Characterization of 4–Hydroxyphenylpyruvate Dioxygenase from Maize", *Pest. Sci.,* 1996, 48(2):109–116.

Herbert et al., "Acetyl–CoA Carboxylase —a Graminicide Target Site", *Pest. Sci.,* 1997, 50(1):67–71.

Stopm in *GUS Protocols: Using the GUS Gene as a Reporter of Gene Expression,* Sean R. Gallagher (ed.), 1992, pp 103–113, Academic Press, San Diego, California.

Chomczynski et al., "Single–Step method of RNA Isolation by Acid Guanidinium Thiocyanate–Phenol–Chloroform Extraction", *Analytical Biochem.,* 1987, 162(1):156–159.

Kedzierski et al., "A Novel Non–Enzymatic Procedure for Removing DNA Template form RNA Transcription Mixtures", *Biotechniques,* 1991, 10(2):210–212 & 214.

Higgins et al., "Fast and sensitive multiple sequence alignments on a microcomputer", *Comput. Appl. Biosci.,* 1989, 5(2):151–153.

Higgins et al., "CLUSTAL: a package for performing multiple sequence alignment on a microcomputer", *Gene,* 1988, 73(1):237–244.

Walkerpeach et al., *Plant Mol. Biol. Manual,* Kluwer Academic Publishers, 1994, B1:1–19,.

Tingey et al., "Chloroplast and Cytosolic Glutamine Synthetase Are Encoded by Homologous Nuclear Genes Which Are Differentially Expressed *in vivo* ", *J. Biol. Chem.,* 1988, 263(20):9651–9657.

Conrad et al., "Compartment–specific accumulation of recombinant immunoglobulins in plant cells: an essential tool for antibody production and immunomodulation of physiological functions and pathogen activity", *Plant Mol. Biol.,* 1998, 38(1 & 2):101–109.

de Feyter et al., "Expressing Ribozymes in Plants", *Methods in Molecular Biology,* vol. 74, Chapter 43, pp. 403–415, Turner, P.C., Humana Press Inc., Totowa, NJ (eds.).

Perriman et al., "Effective ribozyme delivery in plant cells", *Proc. Natl. Acad. Sci. USA,* 1995,92:6175–6179.

* cited by examiner

*Primary Examiner*—W. Gary Jones
*Assistant Examiner*—Janell E. Taylor
(74) *Attorney, Agent, or Firm*—Fish & Richardson, P.C., P.A.

(57) ABSTRACT

Fatty acid desaturase 5' regulatory elements are described, as well as nucleic acid constructs and transgenic plants that include these regulatory elements. Also described are fatty acid desaturase 3' untranslated regions.

47 Claims, 9 Drawing Sheets

TCGACCTGCAGGTCAACGGATCTGGTTTTATGGATACTTTCGTGCACTGGTTTAAGAT
GCAATGTTTGACACATTTCTCAACGTCGGTTGAAAGAGAAATTTGTGCCGAAAACATC
ATTATACATATAGCTACTATCATGAAAATAGTGCATGAATTTTTAAAATTTTGAGTTTTC
ATAATGTATATATGATTACAACAAATGTGAAATATGTATTAGTTTAGTCATTTTTAGATC
GTGAACAAGATGATTCTGAAATTATGTTAGTCTTGGTGAATTATATAGTAAAGTAAATT
ATGGGTATTTTTAGAAATTTGTTTTAGCTTGTTTGTTGTTGTTTTTAATGTATATACAT
CGATTAAGTTGTGTGGAACTTACCTATATTTTGTTGTGCTAGCTATCTAACCATTTTTT
GTTATAACAATAAAATATATCCTTTTTTATCAGCAGCAATAAGATATATTTTTGGGTAAT
TATTATAGTTATATTTAAAAATTTAAATAATATCATACTATTATGTCAAAACTTTGTGATC
TAAACACAAAAACTATTTTACTAAAATTTTCACATAATTCAAGTTATATTATGTATTTTTT
TAATTAAACTTTAGTTTTATCATTTGTTATATGTTTTACTTTTGGTTCTCAATTTTAAAAA
TCTATTATGGTTTTCTATTTTTTTGTAATTTTTTCAAATTTGAAATTTGTGACTTGAACAA
TTATATTTCTTGTAAGATATATATATATATATATATATATATATATATATATATACTGACT
TTCACTGCTTCGTTTTCAACAAAATAATTTAGTTTCTACATAAATATACAGTAATTTTGT
AAGATGATTTTCCTCTTTTAAATTTTTTTGGTTTGGTACCTAACCAAACCGACCCGGTG
TCCGAAGTGCTTAGAGCTAAAAACCCATTCGGTATTTGCCTGGTCCCGTTACCGAAC
CGGACCCATTATTTCGGTTCGGTTTAAGGTGTGGACTCTGTTTTAAGTTAAAAACGTC
CAGCCCTAAGGTAAATTATAAAACATTGGTTGTGTGTCTGTCTCCTCGGTATGGAAAA
CATAATAGAATCCGAACTTACTAGACCAGTACGCGATTTATTTTTCGTCTTACGTCGTA
AGATGTCGAATAAGGAACAAGCAACGTCATTATACATGTTAACCGTATCAAAGGAATC
GAAACAGCCTCATCTTGCGAATCCGGTTATCTTCCATCCTTTTTTCAGGACACTCCGG
TTTACCTTTTTGTTTGTTCGATACGTCACTCCGGTTTAAATCGAATTTAAAAAAAAAAAT
CGGGAAGAGTTAGGAAAAAAAGGAAAATCTCATCTCACCGGCTCACCCTCGACGAC
AAGACAACACCACCCTTAGGGTTAAAAAGGTTTATTTATCTTATTACTAGGGTCGGCC
CGCCCTACGGGCGGGATATTAGTTAATTTGATATTCACTAAATGCTCGAGTTGAAATT
TGTTTTAAGATTTAAGAATTTGGTTATCTGTTATGTCTTACTTATTAGTATGCGGTGGT
ATAGTTGTTTTTCGATTATTCTTGCTTTGGTATTGTATCAAATTAACTAATTGTATAACT
CATAATTATAGATGTACAAATGTAGATTTGTGATAAAGTCTGATGACAATACTGTTTTT
TTTTTAATTTTTATTCATAGTGGAGTGTGCATGTGTCAGAAAGAAGCCTGTAACAACTT
TTATGTTTTTGTGTATGGATTTTAAATATATATTATTTTGTATAATGCATACTTGTTCTAC
AACATTTGCTTGTAGACTAAAAAAATTGTTTTTTATATTTTTAAAAGAGAAAATATTTAG
TCTAGAATATAACATGCACATATGTATTGACTATATATAGAAGTTGAGTGTTATTTTAA
AATAACATATGTATAGAGATTTTTCAACTATTACTTCACTGGCACAAAACATTTATAACT
GTAAATAATTTCTTTTAAAAGCAAAACTAATAAAAGCGTGTACAACAAATGTATTTTGA
TATATATTATATGCATCAAGTTATAAAGGTTGGAAACATTGCAAAACTGTTTGGAGCAA

FIG. 3A

AGTTTTTAACTTCACGATTTTCATCTTGACGTCAGTTCAGTGTCGGCCCTGGCCACAA
GCAGAAGAAGCATGGGCTTCCAGCTGACACGATAATAAGTATTTTCGCGGCCACATA
TTTATAAAAAGTGACTTTAGCCTAGTGGTTCTAAGAGAAATTACCAGTGCTAGAGGTG
CTGGGTTCAATTACCCTTAACTGCATTTATTTATTTTGGCCCTAAATATAAAATGGGAC
ACGTGTCACTCCCAAAACGCACAAATTGATGATGTGGCTTCACGGGAGAGAGGCGAA
CATTTCTTTATATATAGATTATTCTCTTCTCTACTCGTTCCTTCTCCCTTTAATCC
CGATTTCGATTTGTCTTCTCCGATTCGCTCTCTAGACACTCACACAGTAGGGTTTCTA
ATTCGGATCTGTACACCTTTAGCCATGGATGCTCGTAAGAGGGGACGGCCTGAAGCT
GGCTCATTCAACTCCAATGGCGGCGGATTCAAGAAGTCGAAGCAAGGTTAGCTCTTT
CGCTATTCCTCTTACTTTGCTATCTCGAAAGAGTGTTATAGTTCTGTTGTGCTTCACTT
GCTCTGTTAAAGGTTGAAACTTTAGATCTTAATTGATGGATGAATAGTTCCTTTGTTGT
CAATTTGATTTGGGGTAGCGATGATTTCTTCAATTCGAGCTTCGTACTGTTTTTACTCA
ACAAAAGTTTTTGTTTTAGTTATGAGATTCTCTAGGAAATTCAAGTTTGGATCTTTGC
TGCAGTCTTTGATCTGATGCAAATCTAAAGTCCATTAATTTTTCAGTTTAATGATGGAT
GAGCTTTTGATAAGTGATCTTAAAGTTAATCAAGCTTATAGTTCTTTTAACTGTCTTTTG
AGTTTGCTTTAGTTTAATCCCTCTTGTAACATATTATCACCATGCCCAAAGCTTGAGTT
TGCTGTGATTGAATTAGCTTTTTTATGTGTTAGTTATTCATGTGGTAGTTGTTGGTAAA
TAATCCTGAAAATTCTAGAGTAGCAGCTTTGATTTAAGTGTGAAGTTACATATAGATGA
GAATTTATGAATGATATGTATGATTCTAAAAGCAAATATTATTGAGCATCAGCAAAGTC
TTAACTAAAGAAAAACACTTAATCTTTGGAACAGAGATGGAATCTGGTTTAGGAAGCA
AATCGAAGCCATGCACAAAATTTTTCAGGTTATAATCCTTTTTCTTAACTAAATTAATAT
TCAAAATTGTTATTTATAGTCTGAGCTTCAAATTAACAACTAAAAATGTATATGCTAATG
AAGTGATTAGCTCTTATTACAGGTATGTATTATTATTCATGCTGAACCAGTTAAAAAAA
AGTTTCAATATAACAAATATGATATTCGATTATAAATTTAGAAATGTATTGAGCTCAACT
GGTGATTATAGCGTAGAAAATCAATCCACACCTTTTGTTTGAGCTGTGGCAGTAGTTA
AGATATGTGTTGTAGTTTTCTGTTTGGTGGTAAGATATTAGTTATTTTGTGTTTGTATC
ATCATGGTCATATAGTGTCTAGTAAGGTTGTTGCATTACTGAATACTGGTGAACATGT
CCGTCGTAGACAAGCAGTTAGCATAGTTGCTATGTGCCAATTCTTCTGTGTTTCAACT
GTTTGTTCTCTTGTGTCTTCTCAATGCCAATGGTTTTTAACTCTCTTGACATATTTATTA
TGCGTCTGTTGCAGCACTTCTGGCTGTCCTTTTGGTGAGAACTGCCATTTCTTGCACT
TTGTTCCCGGAGGATACAATCCTGTATCACAGATGACAAACATGGGATCACCCATGT
CTCAAGTTTCCAGAAACATGCAAGGATCTGGTGGTGGTGGTGGTGGAGGTCGGTTTT
CGGGGAGAGGAGAGTCAGGGCCTGGCCATGTCTCTAGCTTTGGTGCCTCAGCCACA
GCCAAGATCAGTGTGGATGCTTCCTTGGCAGGCGCAATCATTGGAAAAGGTGGAGT
CTGTTCGAAACAGATATGTCGTCAGACAGGAGCAAAGCTATCGATCCAAGATCACGA
GAGAGATCCCAACCTGAAGAACATTGAGCTTGAAGGAACATTCGAGCAGATAAACGA
AGCGAGCGCAATGGTTAGAGAGCTGATTGGGAGGCTTAATTCCGCATCTAGGAGAC

FIG. 3B

```
CACCTGGTGGCGGTGGTGGCGGGGGTGGGCTTGGTTCTGAAGGGAAACCACATCC
AGGAAGCAACTTCAAGACGAAGATGTGTGAGAGATTCTCTAAAGGAAGCTGTACATT
TGGTGATAGATGTCACTTTGCTCACGGGGAAGCAGAGCTACGCAGGTCATGAATTGC
GCCTAGAGTTACTGGTGAAACAAGTCTCTTTCATTTGTTGTGGTGATTCCTAATATCAT
CTTCTCCTACTTGTTTTTAGTTGTCTTTGTTTTTTGAAACTACAATGTTTAGTTTTCATT
GTCAGTGTAAGTTTTCCCCATTTGGTGTTTTTTTAGAATCTAGTTTGAATTTGAGATGG
GGCAAGCTTGATGAATGATTGGCAAACAGTGGTTAGGATTTGTGTGCTGTCTCTACT
TAATATTTCATGTTTTATCTACTTTATTTTGGTCAGCAAGTTGATGTGTTTCTCTGATGT
GTGTGTGATTATCAGCTTAGATTATTTTGTGAGTATGCTAGACTGTATAACTAATCGTT
GTCGATGTTATAGTTCTCTTATAATGTTTGATAGACTATATAACTAAAAATTCATGTTAT
TAATAGCCGTCGCTGATAGTAACAGCTGAATAAATGAAATGAAATCATGGTAGGTGAT
GATCTTTAAAGAATGTTAAAAATAATGTGTCGTTATAAGCGGTAATGCATAGAAAAACT
CTAATCATCTTAACATAAGAGAGAGCGATAGCTTTAATAAAGTACTTAAATTAATTACT
AGTCGGCAGTCGCTGCCTACTTGTGTACCACCTAAATTAATTTATTATAATATATGACG
AATCTCCAAAGTACATCACACACACTCGGGGCTATTCACGTGATCTCAACCACAATGT
CTGCAGATATTTTTTTAAGTTTTCTTCTCACATGGGAGAAGAAGAAGCCAAGCACGAT
CCTCCATCCTCAACTTTATAGCATTTTTTTCTTTTCTTTCCGGCTACCACTAACTTCTAC
AGTTCTACTTGTGAGTCGGCAAGGACGTTTCCTCATATTAAAGTAAAGACATCAAATA
CCATAATCTTAATGCTAATTAACGTAACGGATGAGTTCTATAACATAACCCAAACTAGT
CTTTGTGAACATTAGGATTGGGTAAACCAATATTTACATTTTAAAAACAAAATACAAAA
AGAAACGTGATAAACTTTATAAAAGCAATTATATGATCACGGCATCTTTTTCACTTTTC
CGTAAATATATATAAGTGGTGTAAATATCAGATATTTGGAGTAGAAAAAAAAAAAAGA
AAAAGAAATATGAAGAGAGGAAATAATGGAGGGGCCCACTTGTAAAAAGAAAGAA
AAGAGATGTCACTCAATCGTCTCACACGGGCCCCGTCAATTTAAACGGCCTGCCTT
CTGCCCAATCGCATCTTACCAGAACCAGAGAGATTCATTACCAAAGAGATAGAGAGA
GAGAGAAAGAGAGGAGACAGAGAGAGAGTTTGAGGAGGAGCTTCTTCGTAGGGTTC
ATCGTTATTAACGTTAAATYTTCATCCCCCCCTAMGTCAGCCAGCTCAAG
```

FIG. 3C

TTCGAGCTCGGTACCCGGGCATCTCTAGAG
TCGACCTGCAGGTCAACGGATCTTTCTTTCGTGCTCACTTGCTGCAGTCTTTGATCTG
ATGCAAATCTAAAGTCAATTAATTTTTCAGTTTAATTGGTGGATGAGCTTTTGATAAGT
GATGTTAAAGTTAGTTTGAGTGCTGTTCGTAGCAAGCTTATTGTTATTTGACTTTCTCT
TGAGTTTCATTATTGCTTTAGTTTAATCCCTTTTGCATTAGCTAGTAACATCTTATCACC
ATGCCCAAAGCTTGAGTTTGCTGTGATTGAATKAGCKTTTTATGTGTTAGTTATKCATG
TGTCTAGTTGTTGGTAAATAATCCTGAAAATTCTAGAGAATATATCTBGCAGCTTTGAT
TTATGTGTGAAGTTACATATAGATGAATTTGATATGTATGATTCTAAAAGCAAATATTAT
TGAACATCAGCAAAGTCTTAACTAAAGAAAAACACTTAATCTTTGGAACAGAGATGGA
ATCTGGTTTAGGAAGCAAATCGAAGCCATGCACAAAATTTTTCAGGTTATAATCCTTTT
CTTAACTAAATTAATATTTAAAATTGTTATTTATAGTCTGAGCTTTAAATTGACAAGTAA
AAATGTATGCTAATGAAGTAGTTAGTTGTTATTACAGGTATGCATCATCCTTCATGCTA
AACAAGTTAAAAAAAAGTTTCAGTATAACAAATATGATATTCACTAGGAACGGAAAAAC
AAATCTGGATTATAAATTTAGAAATATTAAGCTCAACTGGTGATTATAGCTTAGAAAAT
CAATCCACACCTTTTGTTTGAGCTGTGGCAGTAGTTAAGATATGTGTTGTAATTCTCT
GTTTGGTGGTAAGATATTAGTTATTGTGTTTGTATCATCATGGTCATATAGTGTCTAGT
AAGGTTGTTGCATTACTGAATACTGGTGAACATGTCCGTCATAGACAAGCAGTTAGCA
TAGTTGCTATGTGCCAATTCTTCTGTGTTTCAACTGTTTGTTCTCTTGTGTCTTCTCAA
TGCCAATGGTTTTTAACTTTCTGACGTATTTGTTATCCTTCTTTTGCAGCACTTCTGGC
TGTCCTTTTGGTGAGAACTGCCATTTCTTGCACTTTGTTCCCGGAGGATACAATCCTA
TGGCACAGATGACAAACATGGGATCACCCATGTCTCAAGTTTCCAGAAACATGCAAG
GTGGTGGTGGTGGTGGGGGCCGATTTTCGGGGAGAGGAGAGTCTGGACCTGGCCA
CGTCTCTAGCTTTGGTGCCTCAGCCACAGCCAAAATCAGTGTGGATGCTTCCTTGGC
AGGCGCAATCATTGGAAAAGGTGGAGTCTGTTCGAAACAGATATGTCGTCAAACAGG
AGCAAAGCTATCGATCCAAGACCACGAGAGAGATCCCAACCTGAAGAACATTGAGCT
TGAAGGAACATTCGAGCAGATCAACGAAGCGAGCGCAATGGTTAGAGAGCTGATTG
GGAGGCTTAATTCTGCATCTAGGAGACCACCTGGTGGTGGTGGCGGTGGACTTGGT
TCAGAAGGGAAACCGCATCCAGGGAGCAACTTCAAAACGAAGATGTGTGAGAGATTC
TCGAAAGGAAGCTGTACATTTGGTGATAGATGTCACTTTGCACACGGGGAAGCAGAG
CTACGCAGGTCATGAATTGCGCCTAGAGTTGCTGGTGGAGTTAGAGAGTTTGCTGGC
GAAACAAGTCTCTTTCATTTGTTGTGGTGATTCCTAATATCATCTTCTCCTACTTGTTTT
TAGTTGTCTTTGTTTTTTGAGACTACAATGTTTAGTTTTCATTGTCAGTGTAAGTTTTCC
CCATTTGGTGTTTTTTTAGAATCTAGTTTGAATTTGAGATGGGGGGATGCTTGATGAA
TGATTGACAAAACAGTGGTTAGGATTTGTATGCTGTTTCTACTTAATATTTCATGTTTT
CTCTGCTTTATTTTGGTCAGTAAGTTCATGTGTTTCTCTGACATGTGTGTGATTATCAG
CTTTGATTATTTTCCGAGTATGTAGATGTTATAGTTCTCTTATGATAGACAATATAACTA

FIG. 4A

AAAATTCATGTTAATAATAGCCGTCGCTGATAGTAACAGCTGAATAAATGAAATGAAAT
CATGGTAGGTGATGATCTTAAAAAAAATGTTGAAAATAATGTGCGTTGTTACAATAGC
ATCTCCTAACCACTTTTATATATGTCTCTATAATAGCATTTAGATTTAGAAGTAAAATCA
CTGCAATCCTACTTTATTTCTTCCTCTAAAATAAAAATTGTTATTTTCACGGAAATACAT
TCCTTTATAATAAAAACATACTTTTTTATTCACAAAATAATCTTTTAATTTTTTATTTTAA
CAATTATAACCAAAATAAATATTTTTTAATGAAAATGTACTGTTTATATAAATATATAATC
ATACTTTTTATTTACATAATAGTTTCTATAAAAATATTCAGTATAAATAATATCATAGTTT
TATGAATGTTACACTAAATTGGATTGGTTTTCAACTTTCACAAATAAAAGTACTATTTA
TAAAATTAGAAAAAAATATATCAAGACTATTCTTTTTTAGAGGAAGAAATAGAAGAATA
CATTGGAAACAAATCTATCTCTATTATATAGTTTTCCTATTTTAGAAAAAAAAAATAGAG
AAATACATTGGAGATGGTTTAAGCSGTAGTAACACAAAGAAAAACTCTAAATATCTTAA
GMGCATCTCTAATGTACACTTCTGTAATTTCTTCTAAAATAGAGATCTCTATTMTASAG
GTGAAAATGCTCCAATGTATGCCTCTATAATAGAATTCATCTATTTTAAAAGAAAATAT
AGAGAAAATTACTTTTTGCTTTTATATTTAAAGGTGGAAATAAAATATCTCTATATAAA
TAAATAAACTCTATTATACATGTATACATTGGAGCATTTTCACTTTTATAATAGAGTTTT
TTTATTTTAAGAAAAAATATAGAGATAGAAATAGAAATAGAAATAGAGATGAGTTGGAG
ATTAGAAATAGAGATGAGTTTGAGATGTTGTTACGTAAGAAAGAGCTAGAGCTTTAAT
AAAGTACTTAAATTAATTACTAGTCGGCAGTCGCTGCCTACTTGTTTACCACCTAAATT
AATTTATTATAATATATATTACGAATCTCCAAAGTACACATCACACACACTCTACTCAC
GTGATCTCAACCACAATGTCTGCAGATATTTTTTATAGTTTTTTCTCACATGGGAGAGA
AGAAGCCAAGCACGATCCTCCATCCTCAACTTTATAGCATTTTTTTCTTTTCTTTCCGG
CTACCACTTGTGAGTCGAGTCGGCAAGGGCGTTTCCTTATATTAAAGTAAAGACATCA
AATACCATCGTCTTAATGCTAATTAACGTAATTGATGAGTTCTATAACATAATCCAAAC
TAGTCTTTGTGAACATTAGGATTGGGTAAACCAATATTTACATTTTAAAAACAAAATAC
AAAAAGAAACGTGATAAACTTTATAAAAGCAATTATATGATCACTGCATCTTTTCCACT
TTTCCGTAAATAAATACATAAAAGTGCCGTAAATATCAGATATTTGGAGTAGAAAAGTA
ATAAAGAAAAGAAATATGAGGAGAGGGAATAATGGAGGGGGCCCACTTGTAAAAAAG
AAAGAAAAGAGATGTCACTCAATCGTCTCCCACGGGCCCCCGTCAATTTAAACGGCC
TGCCTTCTGCCCAATCGCATCTTATCAGAACCAGACAGATTCATTACCAAAGAGATAG
AGAAAGAGAGAGAGAGAGAGAGAGAGAGAGAGAGTGAGTTTGAGGAGGAGCTTCTTCG
TAGGGTTCATCGTTATTAACGTTAAATCTTCACCCCCTACGTCAGCCAGCTCAAG

FIG. 4B

```
AGCAAAGAAGAAACTGAACCTTTCTCATCTATGATTGTCTTTGTTTTAAGAAGCTATGT
TTCTGTTTCAATAATCTTTAATTATCCATTTTGTTGTGTTTTCTGACATTTTGGCTAAAA
TTATGTGATGTTGGAAGTTAGTGTCTAAAATGTCTTGTGTCTGTATTGTTCTTCTTCTC
ATCGCTGTTATGTTTGGGATCGTTGAAATGTGACTYTCGGACTAGTGAACTCTTGTTC
TCGAACTATCTTAATGTGGATCCCTGAACAGTGTAATGGCTTAGCTTCCTCTGAAACT
ACTATTATGTTCTAGTGAATCTTGACATAAAGCAACTTGTCGTTTCAAGACATACCAAT
GCTTTAAGAAAATGTTTTACTCACCTGAAGTGAACCATAAATCTAATCTTCGTTACAG
TTAAGTTAGTTTGAGTTATTGCGTTGTTTGGTTGGCAGATCACCTTTACTACTCATGTG
GTTCAGTCTCTTTGTAAAAAACTCTATTCTTCTCTTTTAATTTGTAGAAACCTGTCAACA
TAAGCCAAATTCATTTCTTCATATTTATTTGCTTTCAGATTTGTGAGGGAACAAAAGAA
AATAAGACAAATGAATCTTTTTTTTTCTCATTAATGGCAGAAACAACCAAAGAGAGTGT
GACAACAAGAAACAATTGTAGTGAGGAAAAACCAAAGAAAAAAATTGTCTGAAACCA
ACTCGTTGAACATATAAAATAATACGAAAAAATCTTTCATCCAACGGCGAGCGTAATC
TTAGAAGCATTTCCTGTGGACTATCGATGGCCCTGCCTCATCATACTCAGCCTTTGCT
ATCCACATCTGCAATACCAACATTGTGTATCATAGTCAGCTTACAAAACGAGTAACAA
GCAGAAAAGATGATTTACCTGTTGGAAGGTACTGAGTGATGCTAGAATGGATCCTCC
GATCCAGACACTATACTTCCTCTCCGGTGGAGCAACCACCTTAATCTTCATACTACTT
GGAGCAAGAGCAGTAATCTCTTTACTCATCCTATCAGCAATTCCAGGGNAACATCGT
GGTTCCACCACTAAGCACAATGTTTCCATACAAATCCTTCCTGATATCAACATCACAC
TTCATGATCGAATTGTAAGTCGTCTCGTGGATACCAGCAGCTTCCATTCCGACCAAAG
ACGGCTGGAAAAGAACCTCGGGACACCTGAACCTCTCCCCTCCGATGGTGATCACC
TGTCCATCAGGCAACTCGTAGCTCTTGTCGACCTGCAGGCATGCAAGCTTCAGCTGC
TCGAGTTCTATAGTGTCACCTAAATCGTATGTGTATGATACATAAGGTTAT
```

FIG. 5

```
GGATATGATGATGGTGAAAGAACAAAGAAGATATTGTCACGAACCTTTCTCTTGCTGT
CTCTGGTCGTCTTTGTTTTAAGAAGCTATGTTTTCGTTTCAATAATCTTAACTATCCATT
TTGTTGTGTTTCTGACATTTTGGCTAAGTTATGTGATGTGGGACACGTTAGTGTCTAA
AATGTCTCTGTGTCTGTATTGTTCTTCTCATCTGTGACTTTCGGACAACTAAACTCTTG
TTCTCGAACTACCTCAATGTGGCATTAATGAAAGTGTTATTGTTGATTTTAATCTGAAA
CTGCTATTATTTAGTGAATTTTTACATCAGCCAACTTGTTTGTTTAAGACCTACCAATG
GTATAAGAAGGTTTGTGTACTAATGTTCACCATGTCCATAGTGTTAAGACATAACCAT
GATCTTCTGTCCAATTAATTTGCGTCGAGTTATCGTGTTATTTGGCACCTTTACTATGT
TTTTTTGTAAAGAACTCCTTACAGAATAGCTTTTTGTAAAGAACTACGTTTTATCTTTTT
GTAAGAACCTTTTAACAAAAGCCAAATTCATTATTACCTGGCACAAGAAAAAACTCTG
GTTTCTTCCTCTTTCTCTGTTTTTAGATTTGAGGAGGAACATGAAGATGAAGAGRRAK
AACAAATARVTARCRRATCTCTTTTWTYCRTTARSGGSAGAGACACCAAAACAGAGTG
RSRACAAGAAACRGGTGTARTGAGGAAAAACSAAAGAGAAAAGAATATKCTGARGCC
AACTCGTTGAACATATKCAAATARCGAAACAATCTTTCATCCAGNCGGCGAKCGTAAT
CGTAGARGCATTTCCTGTGGACTAKCGATGGCCCTGCCTCATCATASTCGKCCTTTG
CTATCCACATCTGCAAGACCAACRTTGTGTATCATAGTCAGCTTAAAAACGAGTAACA
AGCAGAATCGACAATTTTACCTGTTGGAAGGTACTGAGTGATGCTAGAATANATCCTC
CAATCCAAACACTATACTTCCTCTCCGGTGGAGCAACCACCTTAATCTTCATACTACT
CGGAGCCAAAGCAGTAATCTCCTTACTCATCCTATCANCAATCCCANGGAA
```

PLANT FATTY ACID DESATURASE PROMOTERS

CROSS REFERENCE TO RELATED APPLICATION

This application claims priority from U.S. Provisional Application Serial No. 60/095,317, filed Aug. 4, 1998.

TECHNICAL FIELD

The invention relates to plant regulatory elements that can be used to express various nucleic acid molecules in transgenic plants.

BACKGROUND OF THE INVENTION

An essential element for genetic engineering of plants is the ability to express genes in various plant tissues. Promoter elements contain specific sequences that guide the binding of proteins necessary for formation of a transcriptional complex, and consequently, allow transcription to begin. Constitutive promoters such as the cauliflower mosaic virus (CaMV) 35S and 19S promoters, as well as Agrobacterium derived promoters such as the nopaline synthase and octopine synthase promoter are widely used for expressing genes in transformed plants.

SUMMARY OF THE INVENTION

The invention is based on the identification of regulatory elements of plant fatty acid desaturase genes, which allows any heterologous nucleic acid molecule to be expressed in plant cells and plants. Thus, plants can be produced that have increased nutritional value, a modified fatty acid composition, or a modified carbohydrate, protein, or secondary metabolite content. In addition, the regulatory elements can be used to produce new pharmaceutical products in plants.

In one aspect, the invention features an isolated nucleic acid molecule including a regulatory element of a fatty acid desaturase gene, wherein the regulatory element is located 5' of the fatty acid desaturase gene in a naturally occurring genome. The fatty acid desaturase gene can be, for example, a Brassica fad2D gene or a Brassica fad2F gene.

The invention also features an isolated nucleic acid molecule having the nucleotide sequences of SEQ ID NO:4, SEQ ID NO:5, nucleotides 5113 to 5796 of SEQ ID NO:4, or nucleotides 3197 to 3867 of SEQ ID NO:5, as well as the complementary sequence of such nucleic acid molecules. The nucleic acid molecule also can be at least 100 nucleotides in length (e.g., 400, 600, or 800 nucleotides) and have at least 70% sequence identity (e.g., 80%, 90%, or 95%) to such nucleic acid molecules. In some embodiments, the isolated nucleic acid molecule includes nucleotides 5113 to 5796 of SEQ ID NO:4 or nucleotides 3197 to 3867 of SEQ ID NO:5.

The invention also features a nucleic acid construct. The construct includes a first nucleic acid molecule operably linked to a second nucleic acid molecule heterologous to the first nucleic acid molecule. The first nucleic acid molecule includes a regulatory element of a fatty acid desaturase gene, wherein the regulatory element is located 5' of the fatty acid desaturase gene in a naturally occurring genome. The first nucleic acid molecule promotes expression of the heterologous second nucleic acid molecule, which can encode, for example, a ribozyme or a polypeptide, such as a polypeptide that confers herbicide resistance.

The nucleic acid construct further can include a third nucleic acid molecule operably linked to the 3' end of the second nucleic acid molecule. The third nucleic acid molecule includes a 3' untranslated region of a fatty acid desaturase gene, wherein the 3' untranslated region is located 3' of the fatty acid desaturase gene in a naturally occurring genome. The third nucleic acid molecule can include a nucleic acid molecule having the nucleotide sequence of SEQ ID NO:6, SEQ ID NO:7, nucleotides 1–894 of SEQ ID NO:6, or nucleotides 1–817 of SEQ ID NO:7, as well as the complementary sequence of such molecules. The nucleic acid molecule can be at least 100 nucleotides in length and have at least 70% sequence identity to a nucleic acid molecule having the nucleotide sequence of nucleotides 1–894 of SEQ ID NO:6 or nucleotides 1–817 of SEQ ID NO:7.

The nucleic acid construct further can include a fourth nucleic acid molecule operably linking the first and second nucleic acid molecules, wherein the fourth nucleic acid molecule is a transit peptide or an intron.

In another aspect, the invention features an isolated nucleic acid construct including a first nucleic acid molecule operably linked to a second nucleic acid molecule heterologous to the first nucleic acid molecule. The first nucleic acid molecule comprises a 3' untranslated region of a fatty acid desaturase gene, wherein the 3' untranslated region is located 3' of the fatty acid desaturase gene in a naturally occurring genome.

The invention also features transformed plant cells and transgenic plants. The transformed plant cells and transgenic plants include a nucleic acid construct. The nucleic acid construct includes a regulatory element of a fatty acid desaturase gene operably linked to a heterologous nucleic acid, wherein the regulatory element promotes expression of the heterologous nucleic acid, and wherein the regulatory element is located 5' of the fatty acid desaturase gene in a naturally occurring genome. The transgenic plant can be a dicot (e.g., alfalfa, soybean, rapeseed, or sunflower) or a monocot (e.g., corn, wheat, rye, rice, or sorghum). Seeds from the transgenic plant also are featured.

In another aspect, the invention features plasmid pMB102, represented by ATCC accession number PTA-2536, and plasmid pMB103, represented by ATCC accession number PTA-2535.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 1:
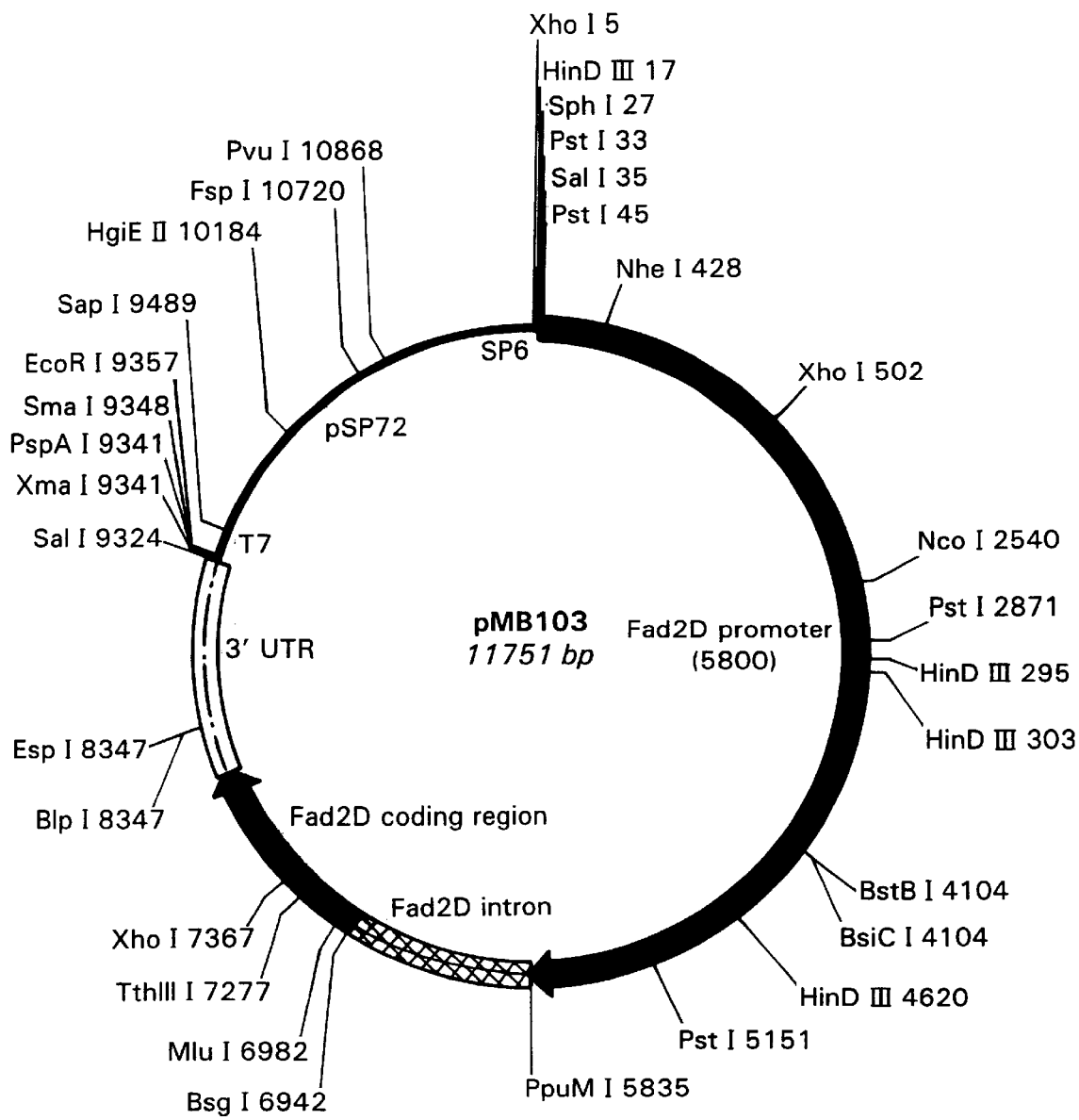
FIG. 1 is a schematic of plasmid pMB103 containing the 1-3A1A SalI genomic DNA fragment from *Brassica napus* 'Bridger' subcloned into the SalI site of pSP72, indicating the positions of the fad2D promoter, fad2D intron, and fad2D 3' untranslated region (UTR) in relation to the fad2D coding sequence.

'Bridger' subcloned into the SalI site of pSP72, indicating the positions of the fad2F promoter, fad2F intron, and fad2F 3'untranslated region (UTR) in relation to the fad2F coding sequence.

FIG. 3 is the nucleotide sequence of the *B. napus* fad2D promoter.

FIG. 4 is the nucleotide sequence of the *B. napus* fad2F promoter.

FIG. 5 is the nucleotide sequence of the *B. napus* fad2D3'untranslated region.

FIG. 6 is the nucleotide sequence of the *B. napus* fad2F3'untranslated region.

DETAILED DESCRIPTION

Regulatory Elements

The invention features an isolated nucleic acid molecule that includes a regulatory element of a gene encoding a fatty acid desaturase (FAD). In a naturally-occurring genome, the regulatory element is located 5' of a fatty acid desaturase (fad) gene, such as a fad1, fad2, or fad3 gene, including introns of such fad genes. For example, the regulatory element may be upstream of fad2D, fad2F, or fad2U genes from Brassica. As used herein, "5' of a fad gene" refers to sequences within 7000 base pairs (bp) of a fad coding region. As used herein, "isolated" refers to a nucleotide sequence corresponding to the regulatory element of a fatty acid desaturase gene, but free of sequences that normally flank one or both sides of the regulatory element in a plant genome. An isolated regulatory element can be, for example, a recombinant DNA molecule, provided one of the nucleic acid sequences normally found flanking that recombinant DNA molecule in a naturally-occurring genome is removed or absent. Thus, isolated regulatory elements include, without limitation, a recombinant DNA that exists as a separate molecule (e.g., a genomic DNA fragment produced by PCR or restriction endonuclease treatment) with no flanking sequences present, as well as a recombinant DNA that is incorporated into a vector, an autonomously replicating plasmid, or into the genomic DNA of a plant as part of a hybrid or fusion nucleic acid molecule.

The coding regions of the fad2D, fad2F, and fad2U genes from *Brassica napus* share 84 to 96% sequence identity at the nucleotide level, as determined by MEGALIGN® (DNASTAR, Madison, Wis.) sequence alignment software using the Clustal algorithm. Fad2D and fad2F genes each encode cytosolic delta-12 desaturases (also called FAD2), which are involved in the enzymatic conversion of oleic acid to linoleic acid. See, U.S. Pat. No. 5,850,026 for sequences of the fad 2D and fad2F genes. The nucleotide sequence of the fad2U gene suggests that it also encodes a cytosolic delta-12 desaturase. See, WO 98/56239 for the sequence of fad2U. Alternatively, fad2U may encode a cytosolic fatty acid hydroxylase or epoxidase, or other enzyme, as the nucleic acids encoding these enzymes share homology with the fad2 family of genes. The fad1 and fad3 genes encode delta-9 and delta-15 desaturases, respectively.

Regulatory elements of the invention were isolated by screening a genomic DNA library from *Brassica napus*, variety 'Bridger' using the coding region of fad2D as a probe. The nucleotide sequence depicted in FIG. 3 (SEQ ID NO:4) is an example of a regulatory element of the invention, and includes approximately 5800 base pairs (bp) upstream of the 5' end of the fad2D intron. The nucleotide sequence depicted in FIG. 4 (SEQ ID NO:5) is a regulatory element that includes approximately 3800 bp upstream of the 5' end of the fad2F intron. A regulatory element of the invention can have a nucleotide sequence that deviates from that shown in SEQ ID NO:4 and SEQ ID NO:5 and retain the ability to promote expression of a nucleic acid molecule. For example, a nucleic acid sequence having at least 70% sequence identity to the nucleotide sequences of SEQ ID NOS:4 and 5 can promote expression of a nucleic acid molecule. In some embodiments, the nucleic acid sequence can have at least 80%, 90%, or 95% sequence identity to the nucleic acid molecule depicted in SEQ ID NOS:4 or 5.

Generally, percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Nucleic acid sequences are aligned and percent identity is calculated by using the Clustal algorithm of MEGALIGN® (DNASTAR, Madison, Wis., 1997) sequence alignment software. In this method, sequences are grouped into clusters by examining the distance between all pairs. Clusters are aligned as pairs, then as groups. A gap penalty of 100 and a gap length penalty of 2 are used in the alignments.

Figure 2:
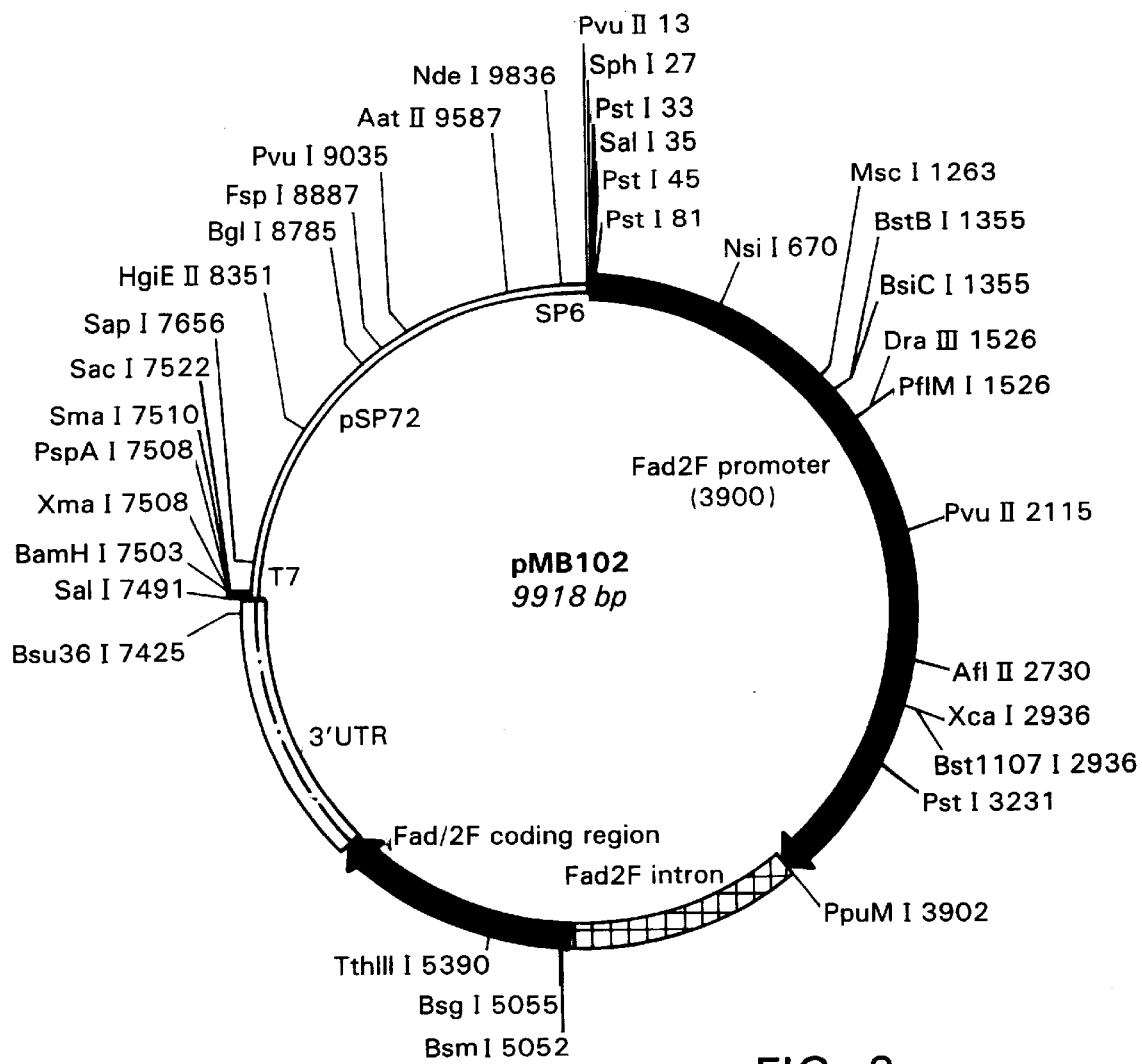
FIG. 2 is a schematic of plasmid pMB102 containing the 1-2A1A SalI genomic DNA fragment from *B. napus*

Fragments of the regulatory element can be made that retain the ability to promote expression of a nucleic acid molecule of interest. FIGS. 1 and 2 provide convenient restriction sites for generating fragments. For example, fragments of the fad2D regulatory element can be made that contain nucleotides 4581 to 5796 of SEQ ID NO:4 or nucleotides 5113 to 5796 of SEQ ID NO:4. Fragments of the fad2F regulatory element can include nucleotides 2081 to 3867 of SEQ ID NO:5 or nucleotides 3197 to 3867 of SEQ ID NO:5. The ability of fragments to promote expression of a nucleic acid molecule can be assayed using the methods described herein. In particular, the fragment can be operably linked to a nucleic acid sequence and used to transiently or stably transform a plant cell. Expression of the gene product encoded by the nucleic acid sequence can be monitored in such transformed plant cells using standard techniques.

In general, fragments of the regulatory element are at least 100 nucleotides in length, e.g., about 200, 400, 600, or 800 nucleotides in length, and have at least 70% sequence identity to the nucleotide sequences of SEQ ID NOS:4 or 5, or to fragments thereof, such as nucleotides 5113 to 5797 of SEQ ID NO:4 or nucleotides 3197 to 3867 of SEQ ID NO:5. In some embodiments, the fragments have at least 80%, 90%, or 95% sequence identity to the nucleotide sequences of SEQ ID NOS:4 or 5, or fragments thereof. Regulatory element fragments may be used as hybridization probes or be used to promote expression of a nucleic acid molecule. Regulatory elements less than 400 bp have been identified which promote expression of nucleic acid molecules in plants. For example, an acyl carrier protein (ACP) promoter retained function after deletion of nucleotides to −290 bp upstream of the initiation of transcription (this region corresponds to 358 nucleotides from the initiation of translation). See, EP-91303098 and U.S. Pat. No. 5,767,363, for a description of the isolation and use of the ACP promoter from *B. napus*. The biotin carboxylase subunit of the plastidial acetyl-CoA carboxylase from Arabidopsis retained a functional promoter after deletion to −140 bp of the initiation of transcription (this region corresponds to 167 nucleotides of the initiation of translation). In addition, seed expression of an enoyl-ACP reductase promoter was unchanged by deleting to −47 bp of the transcription start site, indicating that all elements needed for high level seed expression were present in this small region.

Fragments of the regulatory elements disclosed herein can hybridize under high stringency conditions to the nucleotide sequences of SEQ ID NO:4 or NO:5, or fragments thereof. Hybridization typically involves Southern analysis (Southern blotting). See, for example, sections 9.37–9.52 of Sambrook et al., 1989, *"Molecular Cloning, A Laboratory Manual"*, second edition, Cold Spring Harbor Press, Plainview; N.Y. High stringency conditions can include the use of low ionic strength and high temperature for washing, for example, 0.015 M NaCl/0.0015 M sodium citrate (0.1× SSC), 0.1% sodium dodecyl sulfate (SDS) at 65° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, syndicated sahnon sperm DNA (50 µg/ml), 0.1% SDS, and 10% dextran sulfate at 42° C., with washes at 42° C. in 0.2×SSC and 0.1% SDS.

A regulatory element of the invention can be cloned from the 5' flanking sequences of a genomic fad gene, or can be obtained by other means including chemical synthesis and polymerase chain reaction (PCR) technology. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991).

Nucleic Acid Constructs

Regulatory elements of the invention can be used to express nucleic acid molecules in plants. As used herein, "heterologous nucleic acid molecule" refers to a nucleic acid molecule other than a fatty acid desaturase 5' regulatory element and its associated coding sequence, and includes any exogenous nucleic acid which is partly or entirely heterologous (i.e., foreign) to the plant, or which is homologous to an endogenous nucleic acid molecule of the plant. A regulatory element and a heterologous nucleic acid molecule can be linked in sense or antisense orientation. As used herein, "operably linked" refers to covalent linkage of two or more nucleic acid molecules in a manner such that transcription and translation can be occur, i.e., production of a polypeptide or RNA molecule is facilitated.

Antisense RNA has been used to inhibit plant target genes using an entire cDNA sequence as well as a partial cDNA sequence. There is also evidence that 3' non-coding sequence fragments and 5' coding sequence fragments can play important roles in antisense inhibition. Antisense nucleic acid constructs include a regulatory element of the invention operably linked, in antisense orientation, to a nucleic acid molecule of interest which is heterologous to the regulatory element.

Constructs operably linked in sense orientation can be used to inhibit the expression of an endogenous gene. Co-suppression using a full-length cDNA sequence as well as a partial cDNA sequence are known. See, e.g., U.S. Pat. No. 5,231,020.

Heterologous nucleic acid molecules can encode, for example, ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is well known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., *Proc. Natl. Acad. Sci. USA*, 92(13):6175–6179 (1995); de Feyter, R. and Gaudron, J., *Methods in Molecular Biology*, Vol. 74, Chapter 43, "Expressing Ribozymes in Plants", Edited by Turner, P. C, Humana Press Inc., Totowa, N. J. RNA endoribonucleases such as the one that occurs naturally in *Tetrahymena thermophila*, and which have been described extensively by Cech and collaborators also are useful. See, for example, U.S. Pat. No. 4,987,071.

Heterologous nucleic acid molecules also can encode polypeptides. As used herein, "polypeptide" refers to an amino acid chain, regardless of length or post-translational modification. Polypeptides can include enzymes or fragments thereof that regulate growth, hormone production, photosynthetic efficiency, nutritional value, and oil or protein composition or reporter polypeptides such as green fluorescent protein, neomycin phosphotransferase II, or β-glucuronidase. Polypeptides also can provide, for example, resistance to environmental stresses such as drought and cold, pathogens, insects, or herbicides. *Bacillus thuringiensis* toxin genes can be expressed in plants to provide insect resistance. See, for example, U.S. Pat. No. 5,380,831. Herbicide resistance to glyphosate and glufosinate can be provided by expressing nucleic acid molecules encoding 5-enolpyruvylshikimate-3-phosphate synthase (EPSPS) polypeptides and phosphinothricin acetyl transferase (PAT) polypeptides, respectively. See, for example, U.S. Pat. Nos. 4,940,835 and 5,489,520. In addition, resistance to glyphosate and glufosinate can be provided by expressing a nucleic acid molecule encoding a hygromycin phosphotransferase (HPH) polypeptide or the glpA and glpB genes from Pseudomonas in the plastid of plants. See, for example, WO 99/05265. Resistance to imidazoline type herbicides can be provided by expression of a nucleic acid molecule encoding an acetohydroxyacid synthase polypeptide. See, for example, U.S. Pat. No. 4,761,373. Resistance to cyclohexanedione or aryloxyphenoxypropanoic acid type herbicides can be provided in corn by expression of nucleic acid molecules encoding herbicide resistant acetyl CoA carboxylase polypeptides (ACC1 and ACC2). See, for example, WO 98/08963 and Herbert et al., *Pestic. Sci.*, 1997, 50:67–71. Expression of a protoporphyrinogen oxidase polypeptide resistant to porphyrric herbicides provides herbicide resistance to protoporphyrinogen inhibiting herbicides. See, for example, WO 98/29554. Resistance to benzyoylcyclohexanedione type herbicides can be provided by expression of a nucleic acid molecule encoding herbicide resistant 4-hydroxyphenylpyruvate dioxygenase polypeptides. See, for example, Barta and Boger, *Pestic. Sci.*, 1996, 48(2):109–116; WO 98/02562; and WO 99/24586. Herbicide resistance also can be provided by expression of nucleic acid molecules encoding single chain Fv antibodies that bind herbicide. Expression of single chain Fv antibodies having specific binding affinity for viral coat proteins in, for example, the cytosol of plants, can provide resistance to viral pathogens. See, for example, Conrad and Fiedler, *Plant Mol. Biol.*, 1998, 38(1&2):101–109 and WO 98/42852.

A nucleic acid construct of the invention further can include a nucleic acid molecule encoding a 3' untranslated region (3'UTR), which increases stability of the transcribed sequence by providing for the addition of multiple adenylate ribonucleotides at the 3' end of the transcribed mRNA sequence. The 3' UTR can be, for example, the nopaline synthase (NOS) 3' UTR or the 3' UTR of a fad gene, which in a naturally-occurring genome, is located 3' of the fad coding sequence. As used herein, "3'" refers to sequences 4000 bp or less (e.g, about 2000 bp or less) that are downstream of a fad coding region. As described herein, the 3' UTR of the fad2D and fad2F genes were isolated and have the nucleotide sequences depicted in FIG. 5 (SEQ ID NO:6) and FIG. 6 (SEQ ID NO:7), respectively. A portion of the 3' untranslated regions of fad2D and fad2F were homologous to actin genes of various plant species. In pMB103, the actin-homologous region ends at nucleotide position 8846 (3' end) and starts at nucleotide 9341 (5' end). In pMB102, the actin-homologous region ends at nucleotide position 7007 (3' end) and starts at nucleotide 7491 (5' end). Fragments of the nucleic acid molecules of SEQ ID NOS:6 and 7 can be made, such as a nucleic acid fragment including nucleotides 1–894 of SEQ ID NO:6 or nucleotides 1–817 of SEQ ID NO:7, which exclude the partial actin genes. Additional fragments that are at least 100 nucleotides in length, and which have at least 70% sequence identity to nucleotides 1–894 of SEQ ID NO:6 or nucleotides 1–817 of SEQ ID NO:7, also can be produced and used in constructs of the invention. For example, a 3' UTR of a fad gene can be linked to the 3' end of a heterologous nucleic acid molecule, which can be further linked to any 5' regulatory element, including the 35S CaMV promoter.

Nucleic acid constructs also can contain elements such as inducible elements, intron sequences, enhancer sequences, or targeting sequences. Such elements are not necessary for the function of the heterologous nucleic acid molecule, although they may provide better expression or allow a nucleic acid molecule to be targeted to a particular organelle (e.g., a plastid). For example, the 5' UTR of the small subunit of ribulose bisphosphate carboxylase can be provided for enhanced expression. Nucleic acid molecules encoding a transit peptide from the small subunit of ribulose bisphosphate carboxylase or other plastid targeted proteins can be used to target the encoded product to the plastid. See, for example, U.S. Pat. No. 5,925,806; and Tingey et al., *J. Biol. Chem.*, 1988, 263(20):9651–9657. Suitable introns for use in the invention include the fad2D and fad2F introns. The sequence of the fad2D intron is shown in WO 98/56239.

The timing of expression of a nucleic acid molecule controlled by a 5' regulatory element from a fad gene will be different from that of nucleic acids controlled by the ACP or napin promoters, based on the differential expression of the corresponding native genes. In addition, the level of expression and the regulation of fad 5' regulatory elements will be different from that of napin and ACP promoters. As such, 5' regulatory elements from fad genes may have special advantages over other promoters in regulating the expression of foreign or endogenous genes.

Surprisingly, each of the promoters from the fad2D and fad2F genes express nucleic acid molecules in a number of different plants. As previously identified fad2D mutant genes resulted in changes in oleic acid content in the seeds, but not in the roots or leaves of canola plants, it was expected that fad2D gene expression was specific to plant seeds. In addition, canola plants containing a point mutation in both the fad2D and fad2F genes have stunted roots when grown at low temperatures or in the field, but contain up to 85% oleic acid in the seeds. The roots of such plants exhibit an altered lipid composition similar to the oleic acid content in the seeds. Based on these data, it was thought that fad2F was expressed in both seeds and roots and that fad2D was expressed in seeds. As described herein, however, fad2D is expressed in roots at even higher levels than fad2F (based on RT-PCR analysis). The regulatory elements of the invention can be used to direct the expression or the co-suppression of genes of interest at the appropriate developmental stages and in tissues corresponding to endogenous fad2D and fad2F expression.

Regulatory elements of the invention are similar to the 35S promoter in directing the transient expression of β-glucuronidase (GUS) in Brassica and soybean leaves and in Brassica callus. In Brassica roots and embryo tissues, however, fad2D and fad2F promoters appear to have higher levels of GUS expression than the 35S promoter. In addition, the fad2F promoter can direct the expression of GUS in corn leaves at levels similar to the 35S promoter. This means, in addition to expression in dicot plants, the fad2F promoter can be used to express a gene of interest in monocot plants.

Transgenic Plants

Transgenic plants can be obtained by introducing at least one nucleic acid construct into a plant cell, as described herein. Suitable plants include dicots such as alfalfa, soybean, rapeseed (high erucic and canola), or sunflower, and monocots such as corn, wheat, rye, rice, or sorghum. Seeds produced by a transgenic plant can be grown and selfed (or outcrossed and selfed) to obtain plants homozygous for the construct. Seeds can be analyzed to identify those homozygotes having the desired expression of the construct. Transgenic plants can be entered into a breeding program, e.g., to increase seed, to introgress the novel construct into other lines or species, or for further selection of other desirable traits. Alternatively, transgenic plants can be obtained by vegetative propagation of a transformed plant cell, for those species amenable to such techniques.

As used herein, a transgenic plant also refers to progeny of an initial transgenic plant. Progeny includes descendants of a particular plant or plant line, e.g., seeds developed on an instant plant. Progeny of an instant plant also includes seeds formed on $F_1$, $F_2$, $F_3$, and subsequent generation plants, or seeds formed on $BC_1$, $BC_2$, $BC_3$, and subsequent generation plants.

Transgenic techniques for use in the invention include, without limitation, Agrobacterium-mediated transformation, electroporation and particle gun transformation. Illustrative examples of transformation techniques are described in PCT Application No. 99/04117 (particle bombardment of Brassica) and U.S. Pat. No. 5,188,958 (Agrobacterium). Transformation methods utilizing the Ti and Ri plasmids of Agrobacterium spp. typically use binary type vectors. Walkerpeach, C. et al., in Plant Molecular Biology Manual, S. Gelvin and R. Schilperoort, eds., Kluwer Dordrecht, C1:1–19 (1994). If cell or tissue cultures are used as the recipient tissue for transformation, plants can be regenerated from transformed cultures by techniques known to those skilled in the art.

Transgenic plants of the invention are useful for a variety of commercial and research purposes, as the regulatory elements of the invention can be used to express any heterologous nucleic acid molecule of interest. Transformed plant cells also are useful as they can be continually propagated in culture. Such cultures are useful for the production in vitro of a variety of useful materials, e.g., secondary metabolites and essential oils.

The invention will be further described in the following examples, which do not limit the scope of the invention described in the claims.

EXAMPLES

Example 1

Identification of Promoter Sequences

A genomic DNA library (300,000 plaques) from *B. napus*, variety 'Bridger's, was screened by hybridization with the coding region of fad2D. Approximately 16 positive plaques were identified on the third round of screening and subsequently purified. Phage DNA of the 16 positive plaques was mapped with various restriction enzymes and by Southern analyses using the fad2D coding region as a probe. Positive genomic DNA fragments (generated by SalI digestion and identified by Southern analysis) from two plaques (clones 1-3A1A and 1-2A1A) were subcloned into the pSP72 vector at the SalI site to produce plasmids pMB103 and pMB102, respectively (FIGS. 1 and 2). Plasmids pMB102 and pMB103 were deposited with the American Type Culture Collection, 10801 University Blvd., Manassas, Va., on Oct. 4, 2000 and have ATCC accession numbers PTA-2536 and PTA-2535, respectively. Subcloned SalI DNA fragments in pSP72 were mapped with different restriction enzymes.

The presence of the fad2D and fad2F genes in the subcloned SalI DNA fragments in pMB103 and pMB102 was verified via PCR. Reaction conditions included 5 µl of 10×PCR buffer with $Mg^{2+}$ (Boehringer Mannheim, provided with Taq polymerase), 1 µl of 10 mM dNTP's (Boehringer Mannheim, Catalog #'s 1 051 458, 1 051 440, 1 051 466, and 1 051 482), 1 µl of 10µM Fad2D RT-1 (caucaucaucauACCGCTACGCTGCTGTCCAA, SEQ ID NO:1) or 1 µl of 10 µM Fad2F-RT2 (caucaucaucauCTCTTCCGTTACGCCTTCACGTAG, SEQ ID NO:2), 1 µl 10 µM BS4 (cuacuacuacuaCATAACTTATTGTTGTACCAG, SEQ ID NO:3), 0.5 µl Taq DNA Polymerase (Boehringer Mannheim, Catalog # 1 647 679), 40.5 µl ddH$_2$O, and 1.0 µl of 10 ng/µl DNA template. Samples were heated to 95° C. for 4 minutes, then amplified using 30 cycles of denaturation at 94° C. for 1 minute, annealing at 65° C. for 2 minutes, and extension at 72° C. for 3 minutes, followed by a final extension at 72° C. for 10 minutes. The primer pair of Fad2FRT-1 and BS-4 specifically amplifies the fad2F gene, while Fad2DRT-1 and BS-4 specifically amplify the fad2D gene. Reaction products that were generated were consistent with the 1-2A1A fragment containing the fad2F gene and 1-3A1A containing the fad2D gene.

In addition, 1-2A1A and 1-3A1A clones were sequenced using synthetic primers from the coding regions of fad2D and fad2F. DNA sequencing was done using the ABI PRISM 310 (Perkin Elmer) sequencer, AmpliTaq DNA polymerase, and dye terminators, as described by the manufacturer. The coding sequences in the 1-2A1A and 1-3A1A genomic clones were identical to previously sequenced fad2F and fad2D coding regions, confirming that the 1-2A1A and 1-3A1A fragments contain the fad2F and fad2D genes, respectively. The complete nucleotide sequences of the genomic DNA fragments from each construct were obtained and are presented in FIGS. 3 and 4. An intron was present four nucleotides upstream of the initiation of translation "ATG" codon in both clones.

A SalI and PpuMI restriction enzyme digest of pMB102 and pMB103 was used to produce DNA fragments of about 3.9 kB and about 5.8 kB, respectively, containing the promoter, but free of intron and coding sequences. DNA fragments released by restriction enzyme digestions were resolved in agarose gels and purified as described by the manufacturer (Qiagen). Purified fragments were ligated into the SalI/SmaI sites of pMB160, which contains a GUS-NOS DNA fragment cloned into the XbaI/EcoRI sites of pSP72, to obtain new plasmids pMB168 and pMB166, respectively. DNA ligations were done with T4 DNA ligase as described by the manufacturer (BRL) and then propagated in DH5α bacterial cells. The 5' regulatory elements of the fad genes were placed in pMB160 such that the regulatory elements could drive the expression of GUS.

The nucleotide sequence of the promoter regions of pMB166 and pMB168 were aligned using MEGALIGN® (DNASTAR, Madison, Wis.) sequence alignment software and the Clustal V method and algorithm described by Higgins and Sharp, *Gene*, 1988, 73(1):237–44 and *Comput. Appl. Biosci.*, 1989, 5(2):151–153. A gap penalty of 100 and a gap length penalty of 2 were used for multiple alignments. Pairwise alignment parameters included a Ktupe of 2, a gap penalty of 5, a window of 4, and a diagonal of 4. The alignment of fad2D and fad2F promoters in pMB166 and pMB168, respectively, identified a region with 86.4% identity. This region starts and ends at nucleotides 4940 and 5796 in the fad2D promoter (FIG. 3, SEQ ID NO:4) and at nucleotides 3132 and 3867 in the fad2F promoter (FIG. 4, SEQ ID NO:5). It appears that this conserved region contains all necessary elements for full functionality of both promoters (see Example 3). The fad2D and fad2F intron nucleotide sequence were aligned using the same computer program and parameters. The two introns had 73% identity.

Example 2

RT-PCR Analysis of Fad2F and Fad2D Expression in Different Plant Tissues

RNA STAT-60 RNA Isolation: RNA was isolated from leaves and roots of Brassica napus, variety Westar, plants grown in the greenhouse for 2 weeks, and from seeds collected at 10, 20, 30, 30–50, and 45–55 days after flowering from field grown Brassica napus IMC129. IMC129 is described in U.S. Pat. No. 5,668,299. Samples were stored at −70° C. before RNA extraction. RNA isolation was based on the manufacturer's protocol for RNA STAT-60 (Tel-Test "B" bulletin No.1). Approximately 200 mg of tissue were used per 2 mls of reagent. Tissue was ground with a mortar and pestle under liquid nitrogen, added to reagent, and homogenized using a polytron homogenizer before extraction step. See, Chomczynski and Sacchi, *Anal. Biochem.*, 1987, 162:156–159; and Kedzierski and Porter, *Biotechniques*, 1991, 10:210–214.

Reverse Transcription: The first strand cDNA reaction mix was prepared and contained 10 µl of 5X first strand buffer (BRL), 5 µl of each dNTP (5 mM), 1 µl oligo dT$_{(12-18)}$ primer (0.5 mg/ml), 1 µl $_p$d (N)$_6$primer (0.5 mg/ml), 1 µl RNA (1–2 µg total), and 28 µl dH$_2$O. After incubating the reaction mix at 65° C. for 2 minutes and cooling to 35° C. at room temperature, 2 µl of 100mM DTT, 1 µl RNasin (Promega), and 1 μl Superscript II Reverse Transcriptase (BRL) were added and mixed. The reaction was incubated for an additional 5 min at 25° C., 5 min. at 30° C., and 60 min. at 37° C. PCR was performed by using 2.5 μl of first strand cDNA reaction mix, or 0.5 g of pMB102 or pMB103 DNA constructs, 5.0 μl 10×PCR BufferII (Perkin-Elmer), 2.5 μl each dNTP (5mM), 1.0μl Upstream primer (50 μM total), 1.0 μl Downstream primer (50 μM total), 0.5 μl Amplitaq Polymerase (Perkin-Elmer), and 37.5 μl dH$_2$O (50 μl total). Reaction conditions included 35 cycles of denaturation at 94° C. for 15 sec, annealing at 60° C. for 30 sec, and extension at 72° C. for 60 sec. Primers that were used included the downstream primer BS-4 (SEQ ID NO:3) and either Fad2D-RT1 or Fad2F-RT2 (SEQ ID NOS:1 and 2, respectively) as the upstream primer.

Amplification products were 434 nucleotides for both fad2D and fad2F, and were detected by electrophoresis through an agarose gel and ethidium bromide staining. Specificity of amplified products was verified by digestion with BalI or SspI restriction enzymes. A BalI restriction digest generated fragments of 274 and 160 base pairs in fad2D, while a SspI digest produced fragments of 234 and 200 base pairs in fad2F. RT-PCR data indicated that fad2F and fad2D genes were expressed in all tissues examined, including leaves, roots, and seeds, although the level of fad2D gene expression was higher than the fad2F gene. This data correlates with the analysis of the fad2F and fad2D promoters described below.

Example 3

Fad2D and Fad2F Promoter Analysis

Constructs were prepared which contained the GUS reporter gene without a promoter (pMB160), under the control of a fad2D promoter (pMB166), under the control of fad2D promoter 5' deletions (pMB179 and pMB180), under the control of a fad2F promoter (PMB168), under control of fad2F promoter 5' deletions (pMB167 and pMB176), or under the control of the 35S promoter (pMB146). Table 1 provides a description of each of these constructs.

TABLE 1

Description of Plasmids

| Plamid | Description | Promoter Length (bp) |
|---|---|---|
| pMB103 | 1-3A1A Sal1 genomic DNA fragment isolated from 'Bridger' genomic library, contains the fad2D gene and promoter. This fragment was subcloned at the SalI site of the pSP72 vector. | |
| pMB102 | 1-2A1A Sal I genomic DNA fragment isolated from 'Bridger' genomic library, contains the fad2F gene and promoter. This fragment was subcloned at the Sal I site of the pSP72 vector. | |
| pMB166 | The SalI and PpuMI (blunted) DNA fragment (containing genomic DNA sequence upstream of the fad2D intron) from pMB103 construct was ligated at the SalI and SmaI sites of the pMB160 construct. | 5800 |
| pMB179 | pMB166 construct was digested with PstI and religated to remove upstream promoter region. | 683 |
| pMB180 | pMB166 construct was digested with HindIII and religated to remove upstream promoter region. | 1215 |
| pMB168 | The SalI and PpuMI (blunted) DNA fragment (contains genomic DNA sequence upstream of the Fad2F intron) from pMB102 construct was cloned at the SalI and SmaI sites of the pMB160 construct. | 3800 |

TABLE 1-continued

Description of Plasmids

| | | |
|---|---|---|
| pMB167 | pMB168 construct was digested with PvuII and religated to remove upstream promoter region. | 1786 |
| pMB175 | pMB168 construct was digested with PstI and religated to remove upstream promoter region. | 670 |

Control Plasmids

| | | |
|---|---|---|
| pMB146 | The 35S-GUS-NOS DNA fragment was released from pBI121 binary vector (Clontech) with HindIII and EcoRI digestion, then subcloned into the HindIII and EcoRI sites of SP72. | |
| pMB160 | GUS-NOS DNA fragment was released from pBI121 binary vector (Clontech) with XbaI & EcoRI digestion, then subcloned into the XbaI & EcoRI sites of pSP72. This plasmid does not contain a promoter. | |

The strength of the different promoter-GUS constructs was evaluated based on the ability to drive transient GUS expression in different plant tissues after biolistic transformation. See, PCT Application No. 99/04117 for a description of biolistic transformation of Brassica. The apparatus used for particle bombardment was the Biolistic PDS-1000/He system (Dupont). The procedure for the particle bombardment followed Bio-Rad US/EG Bulletin 1689, using 0.6 μm gold particles. Each bombardment delivered about 2 μg of DNA. After bombardment, the tissues were cultured or kept in a moist environment for 24 hours, as described in PCT Application No. 99/04117, then assayed for GUS expression by staining. A GUS staining method is described by Stopm in *GUS Protocols: Using the GUS Gene as a Reporter of Gene Expression*, Sean R. Gallagher (ed.), 1992, pp 103–13, Academic Press, San Diego, Calif.

Promoter strength was estimated from the GUS staining, using a grading system of 0 to 5. A "0" indicates no blue dots were observed; a "1" indicates 1–10 blue dots were observed; a "2" indicates 11–100 blue dots were observed; a "3" indicates that 101–1000 blue dots were observed; a "4" indicates that 1001–5000 blue dots were observed; and a "5" indicates that >5000 blue dots were observed. From one to four experiments were done for wheat and soybean. Two to eight experiments were done for Brassica species, corn, and sunflower. Table II shows the highest grade observed in the experiments.

Background expression of the GUS gene was evaluated using the pMB160 construct. In the leaves, microspore embryo, and roots of Brassica species, GUS background expression varied from 0 to 1, depending on the tissue examined. GUS background expression was detected in soybean leaves at levels of 1 to 2.

The fad2F promoter (3866bp) in the pMB168 construct transiently expressed GUS in Brassica leaves (*B. napus* and *B. juncea*), roots, microspore embryos, cultured tissues, and cotyledon and hypocotyl at levels graded as 5, 2, 2, 3, and 2, respectively. High GUS expression was observed in soybean leaves (grade 5) and in sunflower leaves (grade 3). The fad2F promoter was able to direct the expression of GUS in corn leaves (a monocot species) at a grade of 1.

Expression of GUS also was obtained when fragments of the fad2F promoter were used. The fad2F promoter from the pMB167 construct, in which the 5' 1800 nucleotides have been deleted (leaving nucleotides 2081–3867 of SEQ ID NO:5), transiently expressed GUS in Brassica leaves, microspore embryos, and cultured tissues reaching grades of 4, 2, and 2, respectively. The fad2F promoter from the pMB175 construct (nucleotides 3197–3867 of SEQ ID NO:5), transiently expressed GUS in Brassica leaves and microspore embryos at levels reaching grades of 3 and 1, respectively. The fad2F promoter in the pMB167 and pMB168 constructs transiently expressed GUS at similar levels, while lower GUS transient expression was detected using the pMB175 construct. These data suggest that the fad2F promoter in pMB168 has all necessary elements to direct the expression of GUS transiently, without reducing the expression levels observed with the full promoter (construct pMB167). Lower GUS activity observed using the pMB175 construct may indicate that an activation element or a region that influences the promoter structure has been removed.

The fad2D promoter (5800 bp) from the pMB166 construct transiently expressed GUS in Brassica leaves, roots, microspore embryos, and cultured tissues at levels reaching grades of 4, 1, 2, and 3, respectively. An expression level of "3" also was obtained in soybean leaves.

Fragments of the fad2D promoter also provided expression of GUS. The fad2D promoter from the pMB179 construct (685 bp, nucleotides 5113–5796 of SEQ ID NO:4) transiently expressed GUS in Brassica leaves up to a grade of 3, depending on the developmental stage of the tissue. The fad2D promoter from the pMB180 construct (1216 bp, nucleotides 4581 to 5796 of SEQ ID NO:4) transiently expressed GUS in Brassica leaves reaching a grade of 4, depending on the developmental stage of the tissue used. The fad2D promoters in the pMB180 and pMB166 constructs transiently expressed GUS at similar levels, suggesting that the promoter in pMB180 has all necessary elements to direct the expression of GUS transiently. A slightly lower GUS activity was observed using the pMB179 construct, suggesting that an activation element or a region that influences the promoter structure may have been removed.

As a comparison, expression of GUS was examined using the 35S promoter. The 35S promoter transiently expressed GUS in Brassica leaves, microspore embryos, and cultured tissues at grades of 5, 1, and 2, respectively. The 35S promoter, however, was not able to express detectable levels of GUS activity in roots (Table II). Expression grades of 2, 5, and 3, were observed in corn and wheat leaves, soybean leaves, and in sunflower leaves, respectively.

Both the fad2D and fad2F promoters in pMB166 and pMB 168 directed the transient expression of a GUS reporter gene in different plant tissues (Table II) at generally similar strengths. RT-PCR analysis described above, however, indicates that fad2D gene expression is higher than fad2F. The discrepancy between the endogenous expression of fad2D and fad2F genes, and the transient analysis of fad2D and fad2F promoters, may be due to differences in the half-lives of the endogenous fad2D and fad2F transcripts. Alternatively, the endogenous expression of fad2D and fad2F transcripts may be influenced by chromosomal structure.

The data described herein provide evidence that fad2D and fad2F promoters are functional and can be used to express genes of interest in all plant tissues, both transiently and after stable transformation.

TABLE II

GUS Assay of Different Promoters Measured by GUS Transient Expression After Particle Bombardment

| Species | Tissue | 35S (pMB146) | Fad2D (pMB166) | Fad2D 5'Δ (pMB179) | Fad2D 5'Δ (pMB180) | Fad2F (pMB168) | Fad2F 5'Δ (pMB167) | Fad2F 5'Δ (pMB175) |
|---|---|---|---|---|---|---|---|---|
| B. juncea | Young leaves | 4 | — | — | — | 5 | — | — |
| B. napus | Cotyledon and Hypocotyl | 3 | — | — | — | 2 | — | — |
|  | Roots | 0 | 1 | — | — | 2 | — | — |
|  | Cell Culture | 2 | 3 | — | — | 3 | 2 | — |
|  | Microspore embryo | 1 | 2 | — | — | 2 | 2 | 1 |
|  | Leaves | 5 | 4 | 3 | 4 | 4 | 4 | 3 |
| Corn | Leaves | 2 | — | — | — | 1 | — | — |
| Soybean | Leaves | 5 | 3 | — | — | 5 | — | — |
| Sunflower | Leaves | 3 | — | — | — | 3 | — | — |
| Wheat | Leaves | 2 | — | — | — | 0 | — | — |

"—" = not tested

Example 4

Promoter Activity in Transgenic Plants

Binary vectors pMB177 and pMB178 were constructed with the GUS reporter gene under the control of the fad2D or fad2F promoter. Similar constructs can be made that contain nucleic acid molecules encoding HPH, NPTII, or PAT.

Stable integration in canola plants is performed with the binary constructs described above using Agrobacterium transformation. Transgenic plants are evaluated for GUS activity in different tissues at different developmental stages. The expression of GUS under the control of fad2D or fad2F promoters is compared with GUS expression without a promoter and with GUS expression under control of a napin promoter using the same vector backbone. Transformants made using HPH, NPTII, or PAT binary constructs are selected on hygromycin, kanamycin, or glufosinate containing media, respectively. Hygromycin, kanamycin, or glufosinate resistant transformants are regenerated into plants and entered into a breeding program.

Other Embodiments

It is to be understood that while the invention has been described in conjunction with the detailed description thereof, the foregoing description is intended to illustrate and not limit the scope of the invention, which is defined by the scope of he appended claims. Other aspects, advantages, and modifications are within the cope of the following claims.

What is claimed is:

1. An isolated nucleic acid molecule selected from the group consisting of:
   (a) a nucleic acid molecule having the nucleotide sequence of SEQ ID NO:4;
   (b) a nucleic acid molecule having the nucleotide sequence of SEQ ID NO:5;
   (c) a nucleic acid molecule having the nucleotide sequence of nucleotides 5113 to 5796 of SEQ ID NO:4;
   (d) a nucleic acid molecule having the nucleotide sequence of nucleotides 3197 to 3867 of SEQ ID NO:5;
   (e) a nucleic acid molecule having a nucleotide sequence complementary to the nucleic acid molecule of (a), (b), (c), or (d); and
   (f) a nucleic acid molecule at least 100 nucleotides in length and having at least 86% sequence identity to said nucleic acid molecule of (a), (b), (c), (d), or (e), wherein said nucleic acid molecule is capable of promoting expression of a heterologous nucleic acid molecule in a transformed plant cell.

2. The isolated nucleic acid molecule of claim 1, wherein said nucleic acid molecule of part (f) is at least 400 nucleotides in length.

3. The isolated nucleic acid molecule of claim 1, wherein said nucleic acid molecule of part (f) is at least 600 nucleotides in length.

4. The isolated nucleic acid molecule of claim 1, wherein said nucleic acid molecule of part (f) is at least 800 nucleotides in length.

5. The isolated nucleic acid molecule of claim 1, wherein said nucleic acid molecule of part (f) is at least 90% identical to said nucleic acid molecule of (a), (b), (c), (d), or (e).

6. The isolated nucleic acid molecule of claim 1, wherein said nucleic acid molecule of part (f) is at least 95% identical to said nucleic acid molecule of (a), (b), (c), (d), or (e).

7. The isolated nucleic acid fragment of claim 1, wherein said nucleic acid fragment comprises nucleotides 5113 to 5796 of SEQ ID NO:4.

8. The isolated nucleic acid fragment of claim 1, wherein said nucleic acid fragment comprises nucleotides 3197 to 3867 of SEQ ID NO:5.

9. The isolated nucleic acid molecule of claim 1, said nucleic acid having the nucleotide sequence of SEQ ID NO:4.

10. The isolated nucleic acid molecule of claim 1, said nucleic acid having the nucleotide sequence of SEQ ID NO:5.

11. A nucleic acid construct comprising a first nucleic acid molecule operably linked to a second nucleic acid molecule heterologous to said first nucleic acid molecule, said first nucleic acid molecule comprising a regulatory element of a fatty acid desaturase gene, wherein said regulatory element comprises a nucleic acid molecule selected from the group consisting of:
   (a) a nucleic acid molecule having the nucleotide sequence of SEQ ID NO:4;
   (b) a nucleic acid molecule having the nucleotide sequence of SEQ ID NO:5;
   (c) a nucleic acid molecule having the nucleotide sequence of nucleotides 5113 to 5796 of SEQ ID NO:4;
   (d) a nucleic acid molecule having a nucleotide sequence of nucleotides 3197 to 3867 of SEQ ID NO:5;
   (e) a nucleic acid molecule having a nucleotide sequence complementary to the nucleic acid molecule of (a), (b), (c), or (d); and
   (f) a nucleic acid molecule at least 100 nucleotides in length and having at least 86% sequence identity to said nucleic acid molecule of (a), (b), (c), (cl), or (e); and wherein said first nucleic acid molecule promotes expression of said second nucleic acid molecule.

12. The nucleic acid construct of claim 11, said construct further comprising a third nucleic acid molecule operably linked to the 3' end of said second nucleic acid molecule, wherein said third nucleic acid molecule comprises a 3' untranslated region of a fatty acid desaturase gene, wherein said 3' untranslated region is located 3' of said fatty acid desaturase gene in a naturally occurring genome.

13. The nucleic acid construct of claim 12, wherein said third nucleic acid molecule is selected from the group consisting of:
   (a) a nucleic acid molecule having the nucleotide sequence of SEQ ID NO:6;

(b) a nucleic acid molecule having the nucleotide sequence of SEQ ID NO:7;

(c) a nucleic acid molecule having the nucleotide sequence of nucleotides 1–894 of SEQ ID NO:6;

(d) a nucleic acid molecule having the nucleotide sequence of nucleotides 1–817 of SEQ ID NO:7;

(e) a nucleic acid molecule at least 100 nucleotides in length and having at least 86% sequence identity to the nucleic acid molecule of (c) or (d); and (f) a nucleic acid nolecule having a nucleotide sequence that is complementary to the nucleic acid molecule of (a), (b)), (c), (d), or (e).

14. The nucleic acid construct of claim 11, said construct further comprising a fourth nucleic acid molecule operably linking said first nucleic acid molecule to said second nucleic acid molecule, wherein said fourth nucleic acid molecule is a transit peptide.

15. The nucleic acid construct of claim 11, said construct further comprising a fourth nucleic acid molecule operably linking said first nucleic acid molecule to said second nucleic acid molecule, wherein said fourth nucleic acid molecule is an intron.

16. The nucleic acid construct of claim 11, wherein said heterologous nucleic acid sequence encodes a ribozyme.

17. The nucleic acid construct of claim 11, wherein said heterologous nucleic acid sequence encodes a polypeptide.

18. The nucleic acid construct of claim 17, wherein said polypeptide confers herbicide resistance.

19. The nucleic acid construct of claim 11, wherein said nucleic acid molecule of part (f) is at least 400 nucleotides in length.

20. The nucleic acid construct of claim 11, wherein said nucleic acid molecule of part (f) is at least 600nucleotides in length.

21. The nucleic acid construct of claim 11, wherein said nucleic acid molecule of part (f) is at least 800 nucleotides in length.

22. The nucleic acid construct of claim 11, wherein said nucleic acid molecule of part (f) is at least 90% identical to said nucleic acid molecule of (a), (b), (c), (d), or (e).

23. The nucleic acid construct of claim 11, wherein said nucleic acid molecule of part (f) is at least 95% identical to said nucleic acid molecule of (a), (b), (c), (d), or (e).

24. A transformed plant cell, said cell containing a nucleic acid construct comprising a regulatory element of a fatty acid desaturase gene operably linked to a heterologous nucleic acid, wherein said regulatory element promotes expression of said heterologous nucleic acid, and wherein said regulatory element comprises a nucleic acid molecule selected from the group consisting of:

(a) a nucleic acid molecule having the nucleotide sequence of SEQ ID NO:4;

(b) a nucleic acid molecule having the nucleotide sequence of SEQ ID NO:5;

(c) a nucleic acid molecule having the nucleotide sequence of nucleotides 5113 to 5796 of SEQ ID NO:4;

(d) a nucleic acid molecule having the nucleotide sequence of nucleotides 3197 to 3867 of SEQ ID NO:5;

(e) a nucleic acid molecule having a nucleotide sequence complementary to the nucleic acid molecule of (a), (b), (c), or (d); and (f) a nucleic acid molecule at least 100 nucleotides in length and having at least 86% sequence identity to said nucleic acid molecule of (a, (b), (c), (d), or (e).

25. The transformed plant cell of claim 24, wherein said nucleic acid molecule of part (f) is at least 400 nucleotides in length.

26. The transformed plant cell of claim 24, wherein said nucleic acid molecule of part (f) is at least 600 nucleotides in length.

27. The transformed plant cell of claim 24, wherein said nucleic acid molecule of part (f) is at least 800 nucleotides in length.

28. The transformed plant cell of claim 24, wherein said nucleic acid molecule of part (f) is at least 90% identical to said nucleic acid molecule of (a), (b), (c), (d), or (e).

29. The transformed plant cell of claim 24, wherein said nucleic acid molecule of part (f) is at least 95% identical to said nucleic acid molecule of (a), (b), (c), (d), or (e).

30. The transformed plant cell of claim 24, said nuclei acid molecule having the nucleotide sequence SEQ ID NO:4.

31. The transformed plant cell of claim 24, said nucleic acid molecule having the nucleotide sequence of SEQ ID NO:5.

32. A transgenic plant comprising at least one nucleic acid construct, said construct comprising a regulatory element of a fatty acid desaturase gene operably linked to a heterologous nucleic acid, wherein said regulatory element promotes expression of said heterologous nucleic acid, and wherein said regulatory element comprises a nucleic acid molecule selected from the group consisting of:

(a) a nucleic acid molecule having the nucleotide sequence of SEQ ID NO:4;

(b) a nucleic acid molecule having the nucleotide sequence of SEQ ID NO:5;

(c) a nucleic acid molecule having the nucleotide sequence of nucleotides 5113 to 5796 of SEQ ID NO:4;

(d) a nucleic acid molecule having the nucleotide sequence of nuclcotides 3197 to 3867 of SEQ ID NO:5;

(e) a nucleic acid molecule having a nucleotide sequence complementary to the nucleic acid molecule of (a), (b), (c), or (d); and (f) a nucleic acid molecule at least 100 nucleotides in length and having at least 86% sequence identity to said nucleic acid molecule of (a, (b), (c), (d), or (e).

33. The transgenic plant of claim 32, wherein said plant is a dicot.

34. The transgenic plant of claim 33, wherein said dicot is alfalfa, soybean, rapeseed, or sunflower.

35. The transgenic plant of claim 32, wherein said plant is a monocot.

36. The transgenic plant of claim 35, wherein said monocot is corn, wheat, rye, rice, or sorghum.

37. A seed from the transgenic plant of claim 32.

38. The transgenic plant of claim 32, wherein said nucleic acid molecule of part (f) is least 400 nucleotides in length.

39. The transgenic plant of claim 32, wherein said nucleic acid molecule of part (f) is at least 600 nucleotides in length.

40. The transgenic plant of claim 32, wherein said nucleic acid molecule of part (f) is at least 800 nucleotides in length.

41. The transgenic plant of claim 32, wherein said nucleic acid molecule of part (f) is at least 90% identical to said nucleic acid molecule of (a), (b), (c), (d), or (e).

42. The transgenic plant of claim 32, wherein said nucleic acid molecule of part (f) is at least 95% identical to said nucleic acid molecule of (a), (b), (c), (d), or (e).

43. The transgenic plant of claim 32, said nucleic acid molecule having the nucleotide sequence of SEQ ID NO:4.

44. The transgenic plan of claim 32, said nucleic acid molecule having the nucleotide sequence of SEQ ID NO:5.

45. Plasmid pMB102, represented by ATCC accession number PTA-2536.

46. Plasmid pMB103, represented by ATCC accession number PTA-2535.

47. An nucleic acid construct comprising a first nucleic acid molecule operably linked to a second nucleic acid molecule heterologous to said first nucleic acid molecule, said first nucleic acid molecule comprising a 3' untranslated region of a fatty acid desaturase gene, wherein said 3' untranslated region is located 3' of said fatty acid desaturase gene in a naturally occurring genome.

* * * * *

UNITED STATES PATENT AND TRADEMARK OFFICE
CERTIFICATE OF CORRECTION

PATENT NO. : 6,537,750 B1
DATED : March 25, 2003
INVENTOR(S) : Basil S. Shorrosh It is certified that error appears in the above-identified patent and that said Letters Patent is hereby corrected as shown below:

Title page,
Item [56], References Cited, FOREIGN PATENT DOCUMENTS,
please add the following:
-- WO 93/11245      06/1993
WO 94/11516      05/1994
WO 96/21022      07/1996
WO 97/10328      03/1997 --.
OTHER PUBLICATIONS, please add the following:
-- Database EMBL 'Online! ID ATO1719, XP002178468

Nishiuchi et al., "Wounding Changes the Spatial Expression Pattern of the Arabidopsis Plastid ω-3 Fatty Acid Desaturase Gene (*FAD7*) through Different Signal Transduction Pathways," Plant Cell, 1997, 9:1701-1712

Slocombe et al., "Temporal and Tissue-Specific Regulation of a *Brassica napus* Stearoyl-Acyl Carrier Protein Desaturase Gene," Plant Physiol., 1994, 104:1167-1176 --.

Column 28,
Line 53, please delete "(cl)" and insert -- (d) -- therefor.
Line 53, please delete second occurrence of "(c)" and insert -- (e) -- therefor.
Line 59, please insert a space between "a" and "3".

Column 29,
Line 10, please delete "nolecule" and insert -- molecule -- therefor.
Line 12, please delete "(b))" and insert -- (b) -- therefor.
Line 34, please insert a space between "600" and "nucleotides".

Column 30,
Line 16, please delete "nuclei" and insert -- nucleic -- therefor.
Line 17, after "sequence" and before "SEQ" please insert -- of --.

UNITED STATES PATENT AND TRADEMARK OFFICE
CERTIFICATE OF CORRECTION

PATENT NO. : 6,537,750 B1
DATED : March 25, 2003
INVENTOR(S) : Basil S. Shorrosh It is certified that error appears in the above-identified patent and that said Letters Patent is hereby corrected as shown below:

<u>Column 32,</u>
Lines 1-7, please cancel claim 47.

Signed and Sealed this

Twenty-seventh Day of January, 2004

JON W. DUDAS
*Acting Director of the United States Patent and Trademark Office*

SEQUENCE LISTING

<160> NUMBER OF SEQ ID NOS: 7

<210> SEQ ID NO 1
<211> LENGTH: 32
<212> TYPE: DNA
<213> ORGANISM: Artifical Sequence
<220> FEATURE:
<223> OTHER INFORMATION: primer

<400> SEQUENCE: 1
caucaucauc auaccgctac gctgctgtcc aa                                           32

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
caucaucauc auctcttccg ttacgccttc acgtag                                       36

<210> SEQ ID NO 3
<211> LENGTH: 33
<212> TYPE: DNA
<213> ORGANISM: Artificial Sequence
<220> FEATURE:
<223> OTHER INFORMATION: primer

<400> SEQUENCE: 3
cuacuacuac uacataactt attgttgtac cag                                          33

<210> SEQ ID NO 4
<211> LENGTH: 5796
<212> TYPE: DNA
<213> ORGANISM: Brassica napus

<400> SEQUENCE: 4
tcgacctgca ggtcaacgga tctggtttta tggatacttt cgtgcactgg tttaagatgc      60
aatgtttgac acatttctca acgtcggttg aaagagaaat ttgtgccgaa acatcatta      120 tacatatagc tactatcatg aaaatagtgc atgaattttt aaaattttga gttttcataa      180
tgtatatatg attacaacaa atgtgaaata tgtattagtt tagtcatttt tagatcgtga      240
acaagatgat tctgaaatta tgttagtctt ggtgaattat atagtaaagt aaattatggg      300 tattttttaga aatttgtttt agcttgtttg ttgttgtttt ttaatgtata tacatcgatt      360
aagttgtgtg gaacttacct atattttgtt gtgctagcta tctaaccatt ttttgttata      420
acaataaaat atatccttttt ttatcagcag caataagata tatttttggg taattattat      480
agttatattt aaaaatttaa ataatatcat actattatgt caaaactttg tgatctaaac      540
acaaaaacta ttttactaaa attttcacat aattcaagtt atattatgta ttttttttaat      600 taaactttag ttttatcatt tgttatatgt tttactttg gttctcaatt ttaaaaatct      660
attatggttt tctattttttt tgtaatttttt tcaaatttga aatttgtgac ttgaacaatt      720
atatttcttg taagatatat atatatatat atatatatat atatatatat atactgactt      780
tcactgcttc gttttcaaca aaataattta gttctacat aaatatacag taattttgta      840
agatgatttt cctcttttaa attttttttgg tttggtacct aaccaaaccg acccggtgtc      900
cgaagtgctt agagctaaaa acccattcgg tatttgcctg gtcccgttac cgaaccggac      960

-continued

```
ccattatttc ggttcggttt aaggtgtgga ctctgtttta agttaaaaac gtccagccct    1020
aaggtaaatt ataaaacatt ggttgtgtgt ctgtctcctc ggtatggaaa acataataga    1080
atccgaactt actagaccag tacgcgattt atttttcgtc ttacgtcgta agatgtcgaa    1140
taaggaacaa gcaacgtcat tatacatgtt aaccgtatca aaggaatcga aacagcctca    1200
tcttgcgaat ccggttatct tccatccttt tttcaggaca ctccggttta cctttttgtt    1260
tgttcgatac gtcactccgg tttaaatcga atttaaaaaa aaaaatcggg aagagttagg    1320
aaaaaaaagg aaaatctcat ctcaccggct caccctcgac gacaagacaa caccacccctt   1380 agggttaaaa aggtttattt atcttattac tagggtcggc ccgccctacg ggcgggatat    1440
tagttaattt gatattcact aaatgctcga gttgaaattt gttttaagat ttaagaattt    1500
ggttatctgt tatgtcttac ttattagtat gcggtggtat agttgttttt cgattattct    1560
tgctttggta ttgtatcaaa ttaactaatt gtataactca taattataga tgtacaaatg    1620
tagatttgtg ataaagtctg atgacaatac tgttttttttt ttaatttta ttcatagtgg    1680 agtgtgcatg tgtcagaaag aagcctgtaa caacttttat gttttttgtgt atggattttta   1740 aatatatatt attttgtata atgcatactt gttctacaac atttgcttgt agactaaaaa    1800
aattgttttt tatattttta aaagagaaaa tatttagtct agaatataac atgcacatat    1860
gtattgacta tatatagaag ttgagtgtta ttttaaaata acatatgtat agagattttt    1920
caactattac ttcactggca caaaacattt ataactgtaa ataatttctt ttaaaagcaa    1980
aactaataaa agcgtgtaca acaaatgtat tttgatatat attatatgca tcaagttata    2040
aaggttggaa acattgcaaa actgtttgga gcaaagtttt taacttcacg attttcatct    2100
tgacgtcagt tcagtgtcgg ccctggccac aagcagaaga agcatgggct tccagctgac    2160
acgataataa gtatttttcgc ggccacatat ttataaaaag tgactttagc ctagtggttc    2220
taagagaaat taccagtgct agaggtgctg ggttcaatta cccttaactg catttatta    2280 ttttggccct aaatataaaa tgggacacgt gtcactccca aaacgcacaa attgatgatg    2340
tggcttcacg ggagagaggc gaacatttct ttatatatat agattattct cttctctcta    2400
ctcgttcctt ctcccttaaa tcccgatttc gatttgtctt ctccgattcg ctctctagac    2460
actcacacag tagggtttct aattcggatc tgtacacctt tagccatgga tgctcgtaag    2520
aggggacggc ctgaagctgg ctcattcaac tccaatggcg gcggattcaa gaagtcgaag    2580
caaggttagc tctttcgcta ttcctcttac tttgctatct cgaaagagtg ttatagttct    2640
gttgtgcttc acttgctctg ttaaaggttg aaactttaga tcttaattga tggatgaata    2700
gttcctttgt tgtcaatttg atttggggta gcgatgattt cttcaattcg agcttcgtac    2760 tgttttttact caacaaaagt ttttgttttt agttatgaga ttctctagga aattcaagtt    2820
tggatctttg ctgcagtctt tgatctgatg caaatctaaa gtccattaat ttttcagttt    2880
aatgatggat gagcttttga taagtgatct taaagttaat caagcttata gttcttttaa    2940
ctgtcttttg agtttgcttt agtttaatcc ctcttgtaac atattatcac catgcccaaa    3000
gcttgagttt gctgtgattg aattagcttt tttatgtgtt agttattcat gtggtagttg    3060
ttggtaaata atcctgaaaa ttctagagta gcagctttga tttaagtgtg aagttacata    3120
tagatgagaa tttatgaatg atatgtatga ttctaaaagc aaatattatt gagcatcagc    3180
aaagtcttaa ctaaagaaaa acacttaatc tttggaacag atatggaatc tggtttagga    3240
agcaaatcga agccatgcac aaaatttttc aggttataat cctttttctt aactaaatta    3300
```

-continued

| | | | | | |
|---|---|---|---|---|---|
| atattcaaaa | ttgttatttta | tagtctgagc | ttcaaattaa | caactaaaaa | tgtatatgct | 3360 |
| aatgaagtga | ttagctctta | ttacaggtat | gtattattat | tcatgctgaa | ccagttaaaa | 3420 |
| aaaagtttca | atataacaaa | tatgatattc | gattataaat | ttagaaatgt | attgagctca | 3480 |
| actggtgatt | atagcgtaga | aaatcaatcc | acaccttttg | tttgagctgt | ggcagtagtt | 3540 |
| aagatatgtg | ttgtagtttt | ctgtttggtg | gtaagatatt | agttattttg | tgtttgtatc | 3600 |
| atcatggtca | tatagtgtct | agtaaggttg | ttgcattact | gaatactggt | gaacatgtcc | 3660 |
| gtcgtagaca | agcagttagc | atagttgcta | tgtgccaatt | cttctgtgtt | tcaactgttt | 3720 |
| gttctcttgt | gtcttctcaa | tgccaatggt | ttttaactct | cttgacatat | ttattatgcg | 3780 |
| tctgttgcag | cacttctggc | tgtccttttg | gtgagaactg | ccatttcttg | cactttgttc | 3840 |
| ccggaggata | caatcctgta | tcacagatga | caaacatggg | atcacccatg | tctcaagttt | 3900 |
| ccagaaacat | gcaaggatct | ggtggtggtg | gtggtggagg | tcggttttcg | gggagaggag | 3960 |
| agtcagggcc | tggccatgtc | tctagctttg | gtgcctcagc | cacagccaag | atcagtgtgg | 4020 |
| atgcttcctt | ggcaggcgca | atcattggaa | aaggtggagt | ctgttcgaaa | cagatatgtc | 4080 |
| gtcagacagg | agcaaagcta | tcgatccaag | atcacgagag | agatcccaac | ctgaagaaca | 4140 |
| ttgagcttga | aggaacattc | gagcagataa | acgaagcgag | cgcaatggtt | agagagctga | 4200 |
| ttgggaggct | taattccgca | tctaggagac | cacctggtgg | cggtggtggc | ggggtgggc | 4260 |
| ttggttctga | agggaaacca | catccaggaa | gcaacttcaa | gacgaagatg | tgtgagagat | 4320 |
| tctctaaagg | aagctgtaca | tttggtgata | gatgtcactt | tgctcacggg | gaagcagagc | 4380 |
| tacgcaggtc | atgaattgcg | cctagagtta | ctggtgaaac | aagtctcttt | catttgttgt | 4440 |
| ggtgattcct | aatatcatct | tctcctactt | gttttagtt | gtctttgttt | tttgaaacta | 4500 |
| caatgtttag | ttttcattgt | cagtgtaagt | tttccccatt | tggtgttttt | ttagaatcta | 4560 |
| gtttgaattt | gagatggggc | aagcttgatg | aatgattggc | aaaacagtgg | ttaggatttg | 4620 |
| tgtgctgtct | ctacttaata | tttcatgttt | tatctacttt | attttggtca | gcaagttgat | 4680 |
| gtgtttctct | gatgtgtgtg | tgattatcag | cttagattat | tttgtgagta | tgctagactg | 4740 |
| tataactaat | cgttgtcgat | gttatagttc | tcttataatg | tttgatagac | tatataacta | 4800 |
| aaaattcatg | ttattaatag | ccgtcgctga | tagtaacagc | tgaataaatg | aaatgaaatc | 4860 |
| atggtaggtg | atgatcttta | aagaatgtta | aaaataatgt | gtcgttataa | gcggtaatgc | 4920 |
| atagaaaaac | tctaatcatc | ttaacataag | agagagcgat | agctttaata | aagtacttaa | 4980 |
| attaattact | agtcggcagt | cgctgcctac | ttgtgtacca | cctaaattaa | tttattataa | 5040 |
| tatatgacga | atctccaaag | tacatcacac | acactcgggg | ctattcacgt | gatctcaacc | 5100 |
| acaatgtctg | cagatatttt | tttaagtttt | cttctcacat | gggagaagaa | gaagccaagc | 5160 |
| acgatcctcc | atcctcaact | ttatagcatt | tttttctttt | ctttccggct | accactaact | 5220 |
| tctacagttc | tacttgtgag | tcggcaagga | cgtttcctca | tattaaagta | aagacatcaa | 5280 |
| ataccataat | cttaatgcta | attaacgtaa | cggatgagtt | ctataacata | acccaaacta | 5340 |
| gtctttgtga | acattaggat | tgggtaaacc | aatatttaca | ttttaaaaac | aaaatacaaa | 5400 |
| aagaaacgtg | ataacttta | taaaagcaat | tatatgatca | cggcatcttt | ttcacttttc | 5460 |
| cgtaaatata | tataagtggt | gtaaatatca | gatatttgga | gtagaaaaaa | aaaaaagaa | 5520 |
| aaaagaaata | tgaagagagg | aaataatgga | ggggcccact | tgtaaaaaag | aaagaaaaga | 5580 |
| gatgtcactc | aatcgtctca | cacgggcccc | cgtcaattta | aacggcctgc | cttctgccca | 5640 |
| atcgcatctt | accagaacca | gagagattca | ttaccaaaga | gatagagaga | gagagaaaga | 5700 |

```
gaggagacag agagagagtt tgaggaggag cttcttcgta gggttcatcg ttattaacgt    5760
taaatyttca tcccccccta mgtcagccag ctcaag                              5796

<210> SEQ ID NO 5
<211> LENGTH: 3867
<212> TYPE: DNA
<213> ORGANISM: Brassica napus

<400> SEQUENCE: 5
tcgacctgca ggtcaacgga tctttctttc gtgctcactt gctgcagtct ttgatctgat      60
gcaaatctaa agtcaattaa ttttcagtt taattggtgg atgagctttt gataagtgat     120
gttaaagtta gtttgagtgc tgttcgtagc aagcttattg ttatttgact ttctcttgag     180
tttcattatt gctttagttt aatccctttt gcattagcta gtaacatctt atcaccatgc     240
ccaaagcttg agtttgctgt gattgaatka gckttttatg tgttagttat kcatgtgtct     300
agttgttggt aaataatcct gaaaattcta gagaatatat ctbgcagctt tgatttatgt     360
gtgaagttac atatagatga atttgatatg tatgattcta aaagcaaata ttattgaaca     420
tcagcaaagt cttaactaaa gaaaacact taatctttgg aacagagatg gaatctggtt     480
taggaagcaa atcgaagcca tgcacaaaat ttttcaggtt ataatccttt tcttaactaa     540
attaatattt aaaattgtta tttatagtct gagctttaaa ttgacaagta aaatgtatg      600 ctaatgaagt agttagttgt tattacaggt atgcatcatc cttcatgcta acaagttaa      660 aaaaagtttt cagtataaca aatatgatat tcactaggaa cggaaaaaca aatctggatt     720
ataaatttag aaatattaag ctcaactggt gattatagct tagaaaatca atccacacct     780
tttgtttgag ctgtggcagt agttaagata tgtgttgtaa ttctctgttt ggtggtaaga     840
tattagttat tgtgtttgta tcatcatggt catatagtgt ctagtaaggt tgttgcatta     900
ctgaatactg gtgaacatgt ccgtcataga caagcagtta gcatagttgc tatgtgccaa     960
ttcttctgtg tttcaactgt ttgttctctt gtgtcttctc aatgccaatg gtttttaact    1020
ttctgacgta tttgttatcc ttcttttgca gcacttctgg ctgtcctttt ggtgagaact    1080
gccatttctt gcactttgtt cccggaggat acaatcctat ggcacagatg acaaacatgg    1140
gatcacccat gtctcaagtt tccagaaaca tgcaaggtgg tggtggtggt ggggccgat     1200 tttcggggag aggagagtct ggacctggcc acgtctctag ctttggtgcc tcagccacag    1260
ccaaaatcag tgtggatgct tccttggcag gcgcaatcat tggaaaaggt ggagtctgtt    1320
cgaaacagat atgtcgtcaa acaggagcaa agctatcgat ccaagaccac gagagagatc    1380
ccaacctgaa gaacattgag cttgaaggaa cattcgagca gatcaacgaa gcgagcgcaa    1440
tggttagaga gctgattggg aggcttaatt ctgcatctag gagaccacct ggtggtggtg    1500
gcggtggact tggttcagaa gggaaaccgc atccaggag caacttcaaa acgaagatgt      1560
gtgagagatt ctcgaaagga agctgtacat ttggtgatag atgtcacttt gcacacgggg    1620
aagcagagct acgcaggtca tgaattgcgc ctagagttgc tggtggagtt agagagtttg    1680
ctggcgaaac aagtctcttt catttgttgt ggtgattcct aatatcatct tctcctactt    1740 gttttagtt gtctttgttt tttgagacta caatgtttag ttttcattgt cagtgtaagt     1800
tttccccatt tggtgttttt ttagaatcta gtttgaattt gagatggggg gatgcttgat    1860
gaatgattga caaacagtg gttaggattt gtatgctgtt tctacttaat atttcatgtt     1920
ttctctgctt tattttggtc agtaagttca gtgtttctc tgacatgtgt gtgattatca     1980
```

-continued

```
gctttgatta ttttccgagt atgtagatgt tatagttctc ttatgataga caatataact    2040
aaaaattcat gttaataata gccgtcgctg atagtaacag ctgaataaat gaaatgaaat    2100
catggtaggt gatgatctta aaaaaaatgt tgaaaataat gtgcgttgtt acaatagcat    2160
ctcctaacca ctttatatata tgtctctata atagcattta gatttagaag taaaatcact    2220
gcaatcctac tttatttctt cctctaaaat aaaaattgtt attttcacgg aaatacattc    2280
ctttataata aaacatact ttttattca caaataatc ttttaattt ttatttaac       2340 aattataacc aaaataaata tttttaatg aaatgtact gtttatataa atatataatc      2400
atacttttta tttacataat agtttctata aaaatattca gtataaataa tatcatagtt    2460
ttatgaatgt tacactaaat tggattggtt ttcaactttc acaaataaaa agtactattt    2520
ataaaattag aaaaaaatat atcaagacta ttctttttta gaggaagaaa tagaagaata    2580
cattggaaac aaatctatct ctattatata gttttcctat tttagaaaaa aaaaatagag    2640
aaatacattg gagatggttt aagcsgtagt aacacaaaga aaaactctaa atatcttaag    2700
mgcatctcta atgtacactt ctgtaatttc ttctaaaata gagatctcta ttmtasaggt    2760
gaaaatgctc caatgtatgc ctctataata gaattcatct attttaaaag aaaatataga    2820
gaaaaattac tttttgcttt tatatttaaa ggtggaaata aaatatctct atataaataa    2880
ataaactcta ttatacatgt atacattgga gcattttcac ttttataata gagtttttt    2940 attttaagaa aaaatataga gatagaaata gaaatagaaa tagagatgag ttggagatta    3000
gaaatagaga tgagtttgag atgttgttac gtaagaaaga gctagagctt taataaagta    3060
cttaaattaa ttactagtcg gcagtcgctg cctacttgtt taccacctaa attaatttat    3120
tataatatat attacgaatc tccaaagtac acatcacaca cactctactc acgtgatctc    3180
aaccacaatg tctgcagata ttttttatag tttttttctca catgggagag aagaagccaa    3240
gcacgatcct ccatcctcaa ctttatagca ttttttttctt ttctttccgg ctaccacttg    3300
tgagtcgagt cggcaagggc gtttccttat attaaagtaa agacatcaaa taccatcgtc    3360
ttaatgctaa ttaacgtaat tgatgagttc tataacataa tccaaactag tctttgtgaa    3420
cattaggatt gggtaaacca atatttacat tttaaaaaca aaatacaaaa agaaacgtga    3480
taaactttat aaaagcaatt atatgatcac tgcatctttt ccactttttcc gtaaataaat    3540 acataaaagt gccgtaaata tcagatattt ggagtagaaa agtaataaag aaaagaaata    3600
tgaggagagg gaataatgga gggggcccac ttgtaaaaaa gaaagaaaag agatgtcact    3660
caatcgtctc ccacgggccc ccgtcaattt aaacggcctg ccttctgccc aatcgcatct    3720
tatcagaacc agacagattc attaccaaag agatagagaa agagagagag agagagagag    3780
agagagagtg agtttgagga ggagcttctt cgtagggttc atcgttatta acgttaaatc    3840 ttcacccct acgtcagcca gctcaag                                         3867
```

<210> SEQ ID NO 6
<211> LENGTH: 1333
<212> TYPE: DNA
<213> ORGANISM: Brassica napus
<220> FEATURE:
<221> NAME/KEY: misc_feature
<222> LOCATION: (1045)...(1045)
<223> OTHER INFORMATION: n=a, g, c, or t

<400> SEQUENCE: 6

```
agcaaagaag aaactgaacc tttctcatct atgattgtct ttgttttaag aagctatgtt      60
tctgtttcaa taatctttaa ttatccattt tgttgtgttt tctgacattt tggctaaaat     120
```

-continued

```
tatgtgatgt tggaagttag tgtctaaaat gtcttgtgtc tgtattgttc ttcttctcat      180
cgctgttatg tttgggatcg ttgaaatgtg actytcggac tagtgaactc ttgttctcga      240
actatcttaa tgtggatccc tgaacagtgt aatggcttag cttcctctga aactactatt      300
atgttctagt gaatcttgac ataaagcaac ttgtcgtttc aagacatacc aatgctttaa      360
gaaaaatgtt ttactcacct gaagtgaacc ataaatctaa tcttcgttac agttaagtta      420
gtttgagtta ttgcgttgtt tggttggcag atcacccttta ctactcatgt ggttcagtct      480 cttttgtaaaa aactctattc ttctctttta atttgtagaa acctgtcaac ataagccaaa      540
ttcatttctt catatttatt tgctttcaga tttgtgaggg aacaaaagaa aataagacaa      600
atgaatcttt ttttttctca ttaatggcag aaacaaccaa agagagtgtg acaacaagaa      660
acaattgtag tgaggaaaaa ccaaagaaaa aaaattgtct gaaaccaact cgttgaacat      720
ataaaataat acgaaaaaat ctttcatcca acggcgagcg taatcttaga agcatttcct      780
gtggactatc gatggccctg cctcatcata ctcagccttt gctatccaca tctgcaatac      840
caacattgtg tatcatagtc agcttacaaa acgagtaaca agcagaaaag atgatttacc      900
tgttggaagg tactgagtga tgctagaatg gatcctccga tccagacact atacttcctc      960
tccggtggag caaccacctt aatcttcata ctacttggag caagagcagt aatctcttta     1020
ctcatcctat cagcaattcc agggnaacat cgtggttcca ccactaagca caatgtttcc     1080
atacaaatcc ttcctgatat caacatcaca cttcatgatc gaattgtaag tcgtctcgtg     1140
gataccagca gcttccattc cgaccaaaga cggctggaaa agaacctcgg gacacctgaa     1200
cctctcccct ccgatggtga tcacctgtcc atcaggcaac tcgtagctct tgtcgacctg     1260
caggcatgca agcttcagct gctcgagttc tatagtgtca cctaaatcgt atgtgtatga     1320
tacataaggt tat                                                         1333

<210> SEQ ID NO 7
<211> LENGTH: 1102
<212> TYPE: DNA
<213> ORGANISM: Brassica napus
<220> FEATURE:
<221> NAME/KEY: misc_feature
<222> LOCATION: (807)...(807)
<223> OTHER INFORMATION: n=a, g, c, or t
<220> FEATURE:
<221> NAME/KEY: misc_feature
<222> LOCATION: (987)...(987)
<223> OTHER INFORMATION: n=a, g, c, or t
<220> FEATURE:
<221> NAME/KEY: misc_feature
<222> LOCATION: (1089)...(1089)
<223> OTHER INFORMATION: n=a, g, c, or t
<220> FEATURE:
<221> NAME/KEY: misc_feature
<222> LOCATION: (1098)...(1098)
<223> OTHER INFORMATION: n=a, g, c, or t

<400> SEQUENCE: 7
ggatatgatg atggtgaaag aacaaagaag atattgtcac gaacctttct cttgctgtct       60
ctggtcgtct ttgttttaag aagctatgtt ttcgtttcaa taatcttaac tatccatttt      120
gttgtgtttt ctgacatttt ggctaagtta tgtgatgtgg acacgttag tgtctaaaat       180 gtctctgtgt ctgtattgtt cttctcatct gtgactttcg gacaactaaa ctcttgttct      240
cgaactacct caatgtggca ttaatgaaag tgttattgtt gattttaatc tgaaactgct      300
attatttagt gaatttttac atcagccaac ttgtttgttt aagacctacc aatggtataa      360
```

-continued

```
gaaggtttgt gtactaatgt tcaccatgtc catagtgtta agacataacc atgatcttct      420
gtccaattaa tttgcgtcga gttatcgtgt tatttggcac ctttactatg tttttttgta      480
aagaactcct tacagaatag ctttttgtaa agaactacgt tttatctttt tgtaagaacc      540 tttaacaaa agccaaattc attattacct ggcacaagaa aaaactctgg tttcttcctc       600
tttctctgtt tttagatttg aggaggaaca tgaagatgaa gagrrakaac aaatarvtar      660
crratctctt ttwtycrtta rsggsagaga caccaaaaca gagtgrsrac aagaaacrgg      720
tgtartgagg aaaaacsaaa gagaaaagaa tatkctgarg ccaactcgtt gaacatatkc      780
aaatarcgaa acaatctttc atccagncgg cgakcgtaat cgtagargca tttcctgtgg     840
actakcgatg gccctgcctc atcatastcg kcctttgcta tccacatctg caagaccaac    900
rttgtgtatc atagtcagct taaaaacgag taacaagcag aatcgacaat tttacctgtt    960
ggaaggtact gagtgatgct agaatanatc ctccaatcca aacactatac ttcctctccg   1020
gtggagcaac caccttaatc ttcatactac tcggagccaa agcagtaatc tccttactca   1080
tcctatcanc aatcccangg aa                                              1102
```